US009198891B2

(12) United States Patent
Cardozo et al.

(10) Patent No.: US 9,198,891 B2
(45) Date of Patent: Dec. 1, 2015

(54) METHOD OF TREATING CANCER BY INHIBITION OF PROTEIN KINASE-LIKE ENDOPLASMIC RETICULUM PROTEIN KINASE

(75) Inventors: Timothy Cardozo, New York, NY (US); Hong Wang, New York, NY (US); David Ron, New York, NY (US)

(73) Assignee: New York University, New York, NY (US)

( * ) Notice: Subject to any disclaimer, the term of this patent is extended or adjusted under 35 U.S.C. 154(b) by 302 days.

(21) Appl. No.: 13/111,769

(22) Filed: May 19, 2011

(65) Prior Publication Data

US 2011/0288083 A1    Nov. 24, 2011

Related U.S. Application Data

(60) Provisional application No. 61/347,206, filed on May 21, 2010.

(51) Int. Cl.
| | | |
|---|---|---|
| *A61K 49/00* | (2006.01) |
| *A61K 31/225* | (2006.01) |
| *A61K 31/24* | (2006.01) |
| *A61K 31/4166* | (2006.01) |
| *A61K 31/4245* | (2006.01) |
| *A61K 31/428* | (2006.01) |
| *A61K 31/433* | (2006.01) |
| *A61K 31/496* | (2006.01) |
| *A61K 31/519* | (2006.01) |
| *A61K 31/536* | (2006.01) |
| *C07D 207/416* | (2006.01) |
| *C07D 239/42* | (2006.01) |
| *C07D 249/12* | (2006.01) |
| *C07D 265/22* | (2006.01) |
| *C07D 277/44* | (2006.01) |
| *C07D 277/54* | (2006.01) |
| *C07D 277/66* | (2006.01) |
| *C07D 307/54* | (2006.01) |
| *C07D 317/60* | (2006.01) |
| *C07D 403/04* | (2006.01) |
| *C07D 403/06* | (2006.01) |

(Continued)

(52) U.S. Cl.
CPC .............. *A61K 31/225* (2013.01); *A61K 31/24* (2013.01); *A61K 31/4166* (2013.01); *A61K 31/428* (2013.01); *A61K 31/4245* (2013.01); *A61K 31/433* (2013.01); *A61K 31/496* (2013.01); *A61K 31/519* (2013.01); *A61K 31/536* (2013.01); *C07D 207/416* (2013.01); *C07D 239/42* (2013.01); *C07D 249/12* (2013.01); *C07D 265/22* (2013.01); *C07D 277/44* (2013.01); *C07D 277/54* (2013.01); *C07D 277/66* (2013.01); *C07D 307/54* (2013.01); *C07D 317/60* (2013.01); *C07D 403/04* (2013.01); *C07D 403/06* (2013.01); *C07D 403/12* (2013.01); *C07D 409/12* (2013.01); *C07D 417/14* (2013.01); *C07D 487/04* (2013.01); *C12Q 1/485* (2013.01); *G06F 19/706* (2013.01); *G06F 19/16* (2013.01)

(58) Field of Classification Search
CPC ..... A61K 51/08; A61K 51/088; A61K 38/00; A61K 38/16; A61K 2123/00; A61K 2121/00; A61K 49/00; A61K 49/0004; A61K 49/0008; A61K 31/225; A61K 31/24; A61K 31/4166; A61K 31/4245; A61K 31/428; A61K 31/433; A61K 31/496; A61K 31/519; A61K 31/536; C07D 403/12; C07D 403/06; C07D 403/04; C07D 317/60; C07D 239/42; C07D 409/12; C07D 417/14; C07D 249/12; C07D 487/04; C07D 265/22; C07D 207/416; C07D 277/44; C07D 277/54; C07D 277/66; C07D 307/54; C12Q 1/485; G06F 19/706; G06F 19/16
USPC ............. 424/1.11, 1.65, 1.69, 9.1, 9.2; 514/1, 514/1.1, 230.5, 254.02, 259.3, 363, 367, 514/389, 534, 548; 530/300, 324, 350; 435/15; 506/8; 544/73, 281, 369; 548/125, 139, 180, 312.1; 560/61, 194; 703/11

See application file for complete search history.

(56) References Cited

U.S. PATENT DOCUMENTS

| | | | |
|---|---|---|---|
| 2002/0116730 A1* | 8/2002 | Allen et al. ..................... 800/18 |
| 2004/0018957 A1 | 1/2004 | Eccleston et al. |

OTHER PUBLICATIONS

Dar et al., "Higher-Order Substrate Recognition of eIF2alpha by the RNA-Dependent Protein Kinase PKR," Cell 122:887-900 (2005).

(Continued)

*Primary Examiner* — D L Jones
(74) *Attorney, Agent, or Firm* — LeClairRyan, a Professional Corporation

(57) ABSTRACT

The present invention relates to a method of identifying compounds useful in inhibiting protein kinase-like endoplasmic reticulum protein kinase (PERK). The method comprises providing a first model comprising PERK active domains, where the said active domains are selected from the group consisting of the peptide spanning from amino acid residue Asp144 to amino acid residue Ser191 of SEQ ID NO: 1 and a peptide comprising the amino acid residue at position 7 of SEQ ID NO: 1, providing one or more candidate compounds, evaluating contact between the candidate compounds and the first model to determine which of the one or more candidate compounds have an ability to bind to and/or fit in the first model, and identifying the compounds which, based on said evaluating, have the ability to bind to and/or fit in the first model as compounds potentially useful for inhibiting PERK. The present invention further relates to compounds that can be used for inhibition of PERK, for example human PERK, and methods related to treatment of PERK-mediated diseases.

9 Claims, 10 Drawing Sheets

(51) Int. Cl.
*C07D 403/12* (2006.01)
*C07D 409/12* (2006.01)
*C07D 417/14* (2006.01)
*C07D 487/04* (2006.01)
*C12Q 1/48* (2006.01)
*G06F 19/00* (2011.01)
*G06F 19/16* (2011.01)

(56) References Cited

OTHER PUBLICATIONS

Nawrocki et al., "Bortezomib Inhibits PKR-Like Endoplasmic Reticulum (ER) Kinase and Induces Apoptosis via ER Stress in Human Pancreatic Cancer Cells," Cancer Res. 65(24):11510-11519 (2005).

O'Connor et al., "Phosphorylation of the Translation Initiation Factor eIF2alpha Increases BACE1 Levels and Promotes Amyloidogenesis," Neuron 69:988-1009 (2008).

GenBank Direct Submission Q9NZJ5, GI: 18203329 (Apr. 20, 2010).

International Search Report and Written Opinion for PCT/US11/37206 (Oct. 17, 2011).

Kim et al., "Cell Death and Endoplasmic Reticulum Stress: Disease Relevance and Therapeutic Opportunities," Nature Reviews 7:1013-1030 (2008).

Wang et al., "Structural Determinants of PERK Inhibitor Potency and Selectivity," Chem. Biol. Drug. Des. 76:480-495 (2010).

\* cited by examiner

```
SEQ_ID_NO_2     ------------------------------------------------------------
SEQ_ID_NO_3     MERATRPGPRALLLLLFLLLGCAAGISAVAPARSLLAPASETVFGLGAAAAPTSAARVPA  60
SEQ_ID_NO_1     ------------------------------------------------------------

SEQ_ID_NO_2     ------------------------------------------------------------
SEQ_ID_NO_3     VATAEVTVEDAEALPAAAGEPESRATEPDDDVELRPGRSLVIISTLDGRIAALDAENDG  120
SEQ_ID_NO_1     ------------------------------------------------------------

SEQ_ID_NO_2     ------------------------------------------------------------
SEQ_ID_NO_3     KKQWDLDVGSGSLVSSSLSKPEVFGNKMIIPSLDGDLFQWDRDRESMEAVPFTVESLLES  180
SEQ_ID_NO_1     ------------------------------------------------------------

SEQ_ID_NO_2     ------------------------------------------------------------
SEQ_ID_NO_3     SYKFGDDVVLVGGKSLITYGLSAYSGKLRYICSALGCRRWDSDEMEEEEDILLLQRTQKT  240
SEQ_ID_NO_1     ------------------------------------------------------------

SEQ_ID_NO_2     ------------------------------------------------------------
SEQ_ID_NO_3     VRAVGPRSGSEKWNFSVGHFELRYIPDMETRAGFIESTFKPGGNKEDSKIISDVEEQEAT  300
SEQ_ID_NO_1     ------------------------------------------------------------

SEQ_ID_NO_2     ------------------------------------------------------------
SEQ_ID_NO_3     MLDTVIKVSVADWKVMAFSRKGGRLEWEYQFCTPIASAWLVRDGKVIPISLFDDTSYTAS  360
SEQ_ID_NO_1     ------------------------------------------------------------

SEQ_ID_NO_2     ------------------------------------------------------------
SEQ_ID_NO_3     EEALGDEEDIVEAARGATENSVYLGMYRGQLYLQSSVRVSEKFPTSPKALESVNGENAII  420
SEQ_ID_NO_1     ------------------------------------------------------------

SEQ_ID_NO_2     ------------------------------------------------------------
SEQ_ID_NO_3     PLPTIKWKPLIHSPSRTPVLVGSDEFDKCLSNDKYSHEEYSNGALSILQYPYDNGYYLPY  480
SEQ_ID_NO_1     ------------------------------------------------------------

SEQ_ID_NO_2     ------------------------------------------------------------
SEQ_ID_NO_3     YKRERNKRSTQITVRFLDSPHYSKNIRKKDPILLLHWWKEIFGTILLCIVATTFIVRRLF  540
SEQ_ID_NO_1     ------------------------------------------------------------

SEQ_ID_NO_2     ------------------------------------------------FEPIQCMGRGGF  12
SEQ_ID_NO_3     HPQPHRQRKESETQCQTESKYDSVSADVSDNSWNDMKYSGYVSRYLTDFEPIQCMGRGGF  600
SEQ_ID_NO_1     ------------------------------------------------FEPIQCXGRGGF  12
                                                                ****** *****

SEQ_ID_NO_2     GVVFEAKNKVDDCNYAIKRIRLPNRELAREKVMREVKALAKLEHPGIVRYFNAWLET---  69
SEQ_ID_NO_3     GVVFEAKNKVDDCNYAIKRIRLPNRELAREKVMREVKALAKLEHPGIVRYFNAWLETPPE  660
SEQ_ID_NO_1     GVVFEAKNKVDDCNYAIKRIRLPNRELAREKVMREVKALAKLEHPGIVRYFNAWLEX---  69
                ********************************************************

SEQ_ID_NO_2     ------------------------------------------------------------
SEQ_ID_NO_3     KWQEEMDEIWLKDESTDWPLSSPSPMDAPSVKIRRMDPFSTKEQIEVIAPSPERSRSFSV  720
SEQ_ID_NO_1     ------------------------------------------------------------

SEQ_ID_NO_2     ------------------------------------------------------------
SEQ_ID_NO_3     GISCGQTSSSESQFSPLEFSGTDCGDNSDSADAAYNLQDSCLTDCEDVEDGTVDGNDEGH  780
SEQ_ID_NO_1     ------------------------------------------------------------

SEQ_ID_NO_2     ------------------------------------------------------------
SEQ_ID_NO_3     SFELCPSEASPYTRSREGTSSSIVFEDSGCCNASSKEEPRGNRLHDCNHYVNKLTDLKCS  840
SEQ_ID_NO_1     ------------------------------------------------------------
```

Figure 7 (contd.):

```
SEQ_ID_NO_2        ----------------------------------------KVYLYIQMQLCRKENLKDWMNR   91
SEQ_ID_NO_3        SSRSSSEATTLSTSPTRPTTLSLDFTKNTVGQLQPSSPKVYLYIQMQLCRKENLKDWMNR  900
SEQ_ID_NO_1        ----------------------------------------KVYLYIQMQLCRKENLKDWMNX   91
                                                           ********************

SEQ_ID_NO_2        RCSLEDREHGVCLHIFLQIAEAVEFLHSKGLMHRDLKPSNIFFTMDDVVKVGDFGLVTAM  151
SEQ_ID_NO_3        RCSLEDREHGVCLHIFLQIAEAVEFLHSKGLMHRDLKPSNIFFTMDDVVKVGDFGLVTAM  960
SEQ_ID_NO_1        RCXXEXREXXVCLHIFLQIAEAVEFLHSKGLMHRDLKPSNIFFTMDDVVKVGDFGLVTAM  151
                   **  * **  **************************************************

SEQ_ID_NO_2        DQDEEEQTVLTPMPAYATHTGQVGTKLYMSPEQIHGNNYSHKVDIFSLGLILFELLYPFS  211
SEQ_ID_NO_3        DQDEEEQTVLTPMPAYATHTGQVGTKLYMSPEQIHGNNYSHKVDIFSLGLILFELLYPFS 1020
SEQ_ID_NO_1        DQDEEEQTVLTPMPAYAXHTGQVGTKLYMSPEQIHGNXYSHKVDIFSLGLILFELLYPFS  211
                   ***************** ******************* **********************

SEQ_ID_NO_2        TLMERVRILTDVRNLKFPLLFTQKYPQEHMMVQDMLSPSPTERPEATDIIENAIFENLEF  271
SEQ_ID_NO_3        TQMERVRILTDVRNLKFPLLFTQKYPQEHMMVQDMLSPSPTERPEATDIIENAIFENLEF 1080
SEQ_ID_NO_1        TXMERVRXLTDVRNLKFPXLFTQKYPXEXXMVQDMLSPSPXERPEAXXIIENAXFEXLXF  271
                   * ***** ********** ******* *  ********* ***** ***** ** * *

SEQ_ID_NO_2        PGKTVLR---------------------------  278
SEQ_ID_NO_3        PGKTVLRQRSRSMSSSGTKHSRQPSCSYSPLPGN 1114
SEQ_ID_NO_1        PGKTVLR---------------------------  278
                   *******
```

Figure 8:

```
SEQ_ID_NO_3    MERATRPGPRALLLLLFLLLGCAAGISAVAPARSLLAPASETVFGLGAAAAPTSAARVP-  59
SEQ_ID_NO_4    MERAISPGLLVRALLLLLLLGLAARTVAAGRARGLPAPTAEAAFGLGAAAAPTSATRVPA  60
               ****  **   .  ***:****.**    *.. **.* **::*:.*************:***

SEQ_ID_NO_3    --AVATAEVTVEDAEALPAAAGEPESRATEPDDDVELRPGRSLVIISTLDGRIAALDAE  117
SEQ_ID_NO_4    AGAVAAAEVTVEDAEALPAAAGEQEPRGPEPDDETELRPGRSLVIISTLDGRIAALDPE  120
                 ***:***********.****** *.*.::******.***************** *

SEQ_ID_NO_3    NDGKKQWDLDVGSGSLVSSSLSKPEVFGNKMIIPSLDGDLFQWDRDRESMEAVPFTVESL  177
SEQ_ID_NO_4    NHGKKQWDLDVGSGSLVSSSLSKPEVFGNKMIIPSLDGALFQWDRDRESMETVPFTVESL  180
               *.**********************************.************.********

SEQ_ID_NO_3    LESSYKFGDDVVLVGGKSLITYGLSAYSGKLRYICSALGCRRWDSDEMEEEEDILLLQRT  237
SEQ_ID_NO_4    LESSYKFGDDVVLVGGKSLTTYGLSAYSGKVRYICSALGCRQWDSDEMEQEEDILLLQRT  240
               *******************.**********.*********:*******:**********

SEQ_ID_NO_3    QKTVRAVGPRSGSEKWNFSVGHFELRYIPDMETRAGFIESTFKPGGNKEDSKIISDVEEQ  297
SEQ_ID_NO_4    QKTVRAVGPRSGNEKWNFSVGHFELRYIPDMETRAGFIESTFKPNENTEESKIISDVEEQ  300
               ************.*******************************. *.:**********

SEQ_ID_NO_3    EATMLDTVIKVSVADWKVMAFSRKGGRLEWEYQFCTPIASAWLVRDGKVIPISLFDDTSY  357
SEQ_ID_NO_4    EAAIMDIVIKVSVADWKVMAFSKKGGHLEWEYQFCTPIASAWLLKDGKVIPISLFDDTSY  360
               **::.*.**************:***:***************:**************

SEQ_ID_NO_3    TASEEALGDEEDIVEAARGATENSVYLGMYRGQLYLQSSVRVSEKFPTSPKALESVNGEN  417
SEQ_ID_NO_4    TSNDDVLEDEEDIVEAARGATENSVYLGMYRGQLYLQSSVRISEKFPSSPKALESVTNEN  420
               *:.::.*.************************************:*****:*******..**

SEQ_ID_NO_3    AIIPLPTIKWKPLIHSPSRTPVLVGSDEFDKCLSNDKYSHEEYSNGALSILQYPYDNGYY  477
SEQ_ID_NO_4    AIIPLPTIKWKPLIHSPSRTPVLVGSDEFDKCLSNDKFSHEEYSNGALSILQYPYDNGYY  480
               *************************************:*********************

SEQ_ID_NO_3    LPYYKRERNKRSTQITVRFLDSPHYSKNIRKKDPILLLHWWKEIFGTILLCIVATTFIVR  537
SEQ_ID_NO_4    LPYYKRERHKRSTQITVRFLDNPHYNKIRKKDPVLLLHWWKEIVATILFCIIATTFIVR   540
               ********:************.***.**.*******:*******:*:**:**********

SEQ_ID_NO_3    RLFHPQPHRQRKESETQCQTESKYDSVSADVSDNSWNDMKYSGYVSRYLTDFEPIQCMGR  597
SEQ_ID_NO_4    RLFHPHPHRQRKESETQCQTENKYDSVSGEANDSSWNDIKNSGYISRYLTDFEPIQCLGR  600
               *****:***************.******.:..*.****:*.***:***********:**

SEQ_ID_NO_3    GGFGVVFEAKNKVDDCNYAIKRIRLPNRELAREKVMREVKALAKLEHPGIVRYFNAWLET  657
SEQ_ID_NO_4    GGFGVVFEAKNKVDDCNYAIKRIRLPNRELAREKVMREVKALAKLEHPGIVRYFNAWLEA  660
               **********************************************************:

SEQ_ID_NO_3    PPEKWQEEMDEIWLKDESTDWPLSSPSPMDAPSVKIRRMDPFSTKEQIEVIAPSPERSRS  717
SEQ_ID_NO_4    PPEKWQEKMDEIWLKDESTDWPLSSPSPMDAPSVKIRRMDPFSTKEHIEIIAPSPQRSRS  720
               *******:**************************************:**:*****:****

SEQ_ID_NO_3    FSVGISCGQTSSSESQFSPLEFSGTDCGDNSDSADAAYNLQDSCLTDCEDVEDGTVDGND  777
SEQ_ID_NO_4    FSVGISCDQTSSSESQFSPLEFSGMDHEDISESVDAAYNLQDSCLTDCD-VEDGTMDGND  779
               *******.****************.*  *.:*.*************. *****:****

SEQ_ID_NO_3    EGHSFELCPSEASPYTRSREGTSSSIVFEDSGCGNASSKEEPRGNRLHDGNHYVNKLTDL  837
SEQ_ID_NO_4    EGHSFELCPSEASPYVRSRERTSSSIVFEDSGCDNASSKEEPKTNRLHIGNHCANKLTAF  839
               ***************.****.************ *******: .****.***.***** :

SEQ_ID_NO_3    KCSSSRSSSEATTLSTSPTRPTTLSLDFTKNTVGQLQPSSPKVYLYIQMQLCRKENLKDW  897
SEQ_ID_NO_4    KPTSSKSSSEAT-LSISPPRPTTLSLDLTKNTTEKLQPSSPKVYLYIQMQLCRKENLKDW  898
               * :**:******  ** **.*******:****.::**************************

SEQ_ID_NO_3    MNRRCSLEDREHGVCLHIFLQIAEAVEFLHSKGLMHRDLKPSNIFFTMDDVVKVGDFGLV  957
SEQ_ID_NO_4    MNGRCTIEERERSVCLHIFLQIAEAVEFLHSKGLMHRDLKPSNIFFTMDDVVKVGDFGLV  958
               ** **.: *: :**:***********************************************

SEQ_ID_NO_3    TAMDQDEEEQTVLTPMPAYATHTGQVGTKLYMSPEQIHGNNYSHKVDIFSLGLILFELLY  1017
SEQ_ID_NO_4    TAMDQDEEEQTVLTPMPAYARHTGQVGTKLYMSPEQIHGNSYSHKVDIFSLGLILFELLY  1018
               ********************.*******************.*******************
```

Figure 8 (contd.):

```
SEQ_ID_NO_3    PFSTQMERVRILTDVRNLKFPLLFTQKYPQEHMMVQDMLSPSPTERPEATDIIENAIFEN  1077
SEQ_ID_NO_4    PFSTQMERVRTLTDVRNLKFPPLFTQKYPCEYVMVQDMLSPSPMERPEAINIIENAVFED  1078
               **********  ********** ******* *::********** *****  :*****:**:

SEQ_ID_NO_3    LEFPGKTVLRQRSRSMSSSGTKHSRQPSCSYSPLPGN  1114
SEQ_ID_NO_4    LDFPGKTVLRQRSRSLSSSGTKHSRQSNNSHSPLPSN  1115
               *:************:**********:.. *:****.*
```

METHOD OF TREATING CANCER BY INHIBITION OF PROTEIN KINASE-LIKE ENDOPLASMIC RETICULUM PROTEIN KINASE

This application claims the benefit of U.S. Provisional Patent Application Ser. No. 61/347,206, filed May 21, 2010, which is hereby incorporated by reference in its entirety.

This invention was made with government under National Institutes of Health grant project numbers IDP2OD004631-01, 5R01DK075311-04, and 5R37DK047119-16. The government has certain rights in this invention.

FIELD OF THE INVENTION

The present invention relates to a method of treating cancer by inhibition of protein kinase-like endoplasmic reticulum protein kinase (PERK).

BACKGROUND OF THE INVENTION

Proteins fold into their native conformation and undergo a series of post-translational modifications in the endoplasmic reticulum (ER) as part of the normal process of cellular homeostasis. Disruption of any of these processes, for example, accumulation of unfolded or misfolded proteins in the ER, results in ER stress. Cells respond to ER stress by activation of the unfolded protein response (UPR) pathway. Multiple studies support the central role for UPR activation in tumor progression (Bi et al., "ER Stress-regulated Translation Increases Tolerance to Extreme Hypoxia and Promotes Tumor Growth," *EMBO J* 24: 3470-81 (2005); Koumenis et al., "Regulation of Protein Synthesis by Hypoxia via Activation of the Endoplasmic Reticulum Kinase PERK and Phosphorylation of the Translation Initiation Factor eIF2α," *Mol Cell Biol* 22: 7405-16 (2002); Ameri et al., "Anoxic Induction of ATF-4 Through HIF-1-independent Pathways of Protein Stabilization in Human Cancer Cells," *Blood* 103: 1876-82 (2004); Romero-Ramirez et al., "XBP1 is Essential for Survival Under Hypoxic Conditions and is Required for Tumor Growth," *Cancer Res* 64: 5943-7 (2004); Shuda et al., "Activation of the ATF6, XBP1 and grp78 Genes in Human Hepatocellular Carcinoma: A Possible Involvement of the ER Stress Pathway in Hepatocarcinogenesis," *J Hepatol* 38: 605-14 (2003); Blais et al., "Novel Therapeutic Target: The PERKs of Inhibiting the Integrated Stress Response," *Cell Cycle* 5: 2874-7 (2006)). In addition, emerging evidence indicates that prolonged activation of the UPR can be detrimental to neurons and thus mediates neurodegeneration in Alzheimer's disease pathogenesis (Hoozemans et al., "The Unfolded Protein Response is Activated in Alzheimer's Disease," *Acta Neuropathol.* 110:165-72 (2005); Hoozemans et al., "The Unfolded Protein Response is Activated in Pretangle Neurons in Alzheimer's Disease Hippocampus," *Am. J Pathol.* 174:1241-51 (2009); Unterberger et al., "Endoplasmic Reticulum Stress Features are Prominent in Alzheimer Disease but Not in Prion Diseases In Vivo," *J. Neuropathol. Exp. Neurol.* 65:348-57 (2006); Chang et al., "Phosphorylation of Eukaryotic Initiation Factor-2α (eIF2a) is Associated With Neuronal Degeneration in Alzheimer's Disease," *Neuroreport.* 13:2429-32 (2002); O'Connor et al., "Phosphorylation of the Translation Initiation Factor eIF2α Increases BACE1 Levels and Promotes Amyloidogenesis," *Neuron* 60:988-1009 (2008); Kim et al., "Cell Death and Endoplasmic Reticulum Stress: Disease Relevance and Therapeutic Opportunities," *Nat. Rev. Drug Discov.* 7(12):1013-30 (2008)).

PKR-like ER protein kinase (PERK), one of the three identified UPR transducers, is a kinase that phosphorylates a single known substrate eIF2α, leading to lower levels of translation initiation, which in turn globally reduces the load of newly synthesized proteins in the ER (Bi et al., "ER Stress-regulated Translation Increases Tolerance to Extreme Hypoxia and Promotes Tumor Growth," *EMBO J* 24:3470-81 (2005); Koumenis et al., "Regulation of Protein Synthesis by Hypoxia via Activation of the Endoplasmic Reticulum Kinase PERK and Phosphorylation of the Translation Initiation Factor eIF2α," *Mol Cell Biol* 22: 7405-16 (2002); Shi et al., "Identification and Characterization of Pancreatic Eukaryotic Initiation Factor 2 A-Subunit Kinase, PEK, Involved in Translational Control," *Mol Cell Biol* 18:7499-509 (1998); Harding et al., "Regulated Translation Initiation Controls Stress-Induced Gene Expression in Mammalian Cells," *Mol Cell* 6:1099-108 (2000)). PERK is a Ser/Thr protein kinase, and its catalytic domain shares substantial homology to other eIF2α family kinases (Harding et al., "Protein Translation and Folding are Coupled by an Endoplasmic-reticulum Resident Kinase," *Nature* 397:271-274 (1999)). PERK oligomerization causes its autophosphorylation and kinase domain activation. PERK then phosphorylates and inactivates eIF2α, shutting down mRNA translation and thereby reducing the protein load on the ER (Harding et al., "PERK is Essential for Translational Regulation and Cell Survival During the Unfolded Protein Response," *Mol Cell* 5:897-904 (2000)). In addition, PERK-mediated eIF2α phosphorylation also induces the transcriptional activation to improve protein folding capacity, thereby further promoting cell survival (Lu et al., "Translation Reinitiation at Alternative Open Reading Frames Regulates Gene Expression in an Integrated Stress Response," *J Cell Biol* 167:27-33 (2004); Wu et al., "From Acute ER Stress to Physiological Roles of the Unfolded Protein Response," *Cell Death Differ* 13:374-84 (2006)). Among this group of three prominent UPR transducers which includes XBP1 and ATF6, PERK may have a broader range of cellular effects than other transducers, perhaps due to its role in regulating the general translation rate through the phosphorylation of eIF2α (Blais et al., "Novel Therapeutic Target: The PERKs of Inhibiting the Integrated Stress Response," *Cell Cycle* 5:2874-7 (2006)). Indeed, eIF2α phosphorylation appears to account for the entire range of the protective effects of PERK under ER stress (Lu et al., "Cytoprotection by Pre-emptive Conditional Phosphorylation of Translation Initiation Factor 2," *EMBO J* 23:169-79 (2004)). Hypoxia, a common feature in solid tumors, results in PERK activation, which protects tumor cells from hypoxic stress (Koumenis et al., "Regulation of Protein Synthesis by Hypoxia via Activation of the Endoplasmic Reticulum Kinase PERK and Phosphorylation of the Translation Initiation Factor eIF2α," *Mol Cell Biol* 22:7405-16 (2002); Koritzinsky et al., "Gene Expression During Acute and Prolonged Hypoxia is Regulated by Distinct Mechanisms of Translational Control," *EMBO J* 25:1114-25 (2006)).

Drug discovery aimed at a particular molecular target like PERK theoretically has three components: 1) screening to identify lead compounds; 2) preclinical testing of lead compounds, including studies of their effects in animals and 3) clinical testing and approval of the drug.

Combinatorial chemistry is a recent addition to the toolbox of chemists and represents a field of chemistry dealing with the synthesis of a large number of chemical entities for the purposes of screening phase of drug discovery. This is generally achieved by condensing a small number of reagents together in all combinations defined by a given reaction sequence. Advances in this area of chemistry include the use of chemical software tools and advanced computer hardware which has made it possible to consider possibilities for synthesis in orders of magnitude greater than the actual synthesis of the library compounds. The concept of "virtual library" is used to indicate a collection of candidate structures that would theoretically result from a combinatorial synthesis involving reactions of interest and reagents to effect those reactions. It is from this virtual library that relevant compounds are selected to be actually synthesized.

Computer-aided drug design is now widely recognized as a viable alternative and complement to the high-throughput screening (Marrero-Ponce et al., "TOMOCOMD-CARDD, A Novel Approach for Computer-Aided 'Rational' Drug Design: I. Theoretical and Experimental Assessment of a Promising Method for Computational Screening and in silico Design of New Anthelmintic Compounds," *J Comput Aided Mol Des* 18:615-34 (2004)). Drug discovery has moved toward more rational drug design strategies based on the increasing understanding of the fundamental principles of protein-ligand interactions, leading to many successes and an increased reliance on computational approaches (Chao et al., "Computer-aided Rational Drug Design: A Novel Agent (SR13668) Designed to Mimic the Unique Anticancer Mechanisms of Dietary Indole-3-carbinol to Block Akt Signaling," *J Med Chem* 50:3412-5 (2007); Zotchev et al., "Rational Design of Macrolides by Virtual Screening of Combinatorial Libraries Generated Through in silico Manipulation of Polyketide Synthases," *J Med Chem* 49:2077-87 (2006); Zauhar et al., "Shape Signatures: A New Approach to Computer-Aided Ligand- and Receptor-based Drug Design," *J Med Chem* 46:5674-90 (2003); Grassy et al., "Computer-assisted Rational Design of Immunosuppressive Compounds," *Nat Biotechnol* 16:748-52 (1998)).

For example, Project Library (MDL Information Systems, Inc., San Leandro, Calif.) is said to be a desktop software system which supports combinatorial research efforts (A. W. Czaniik and S. H. DeWitt, *Practical Guide to Combinatorial Chemistry*, ACS, Washington, D.C. (1997)). The software includes an information-management module for the representation and search of building blocks, individual molecules, complete combinatorial libraries, and mixtures 4Q of molecules, and other modules for computational support for tracking mixture and discrete-compound libraries. Similarly, Molecular Diversity Manager (Tripos, Inc., St. Louis, Mo.) is said to be a suite of software modules for the creation, selection, and management of compound libraries (A. W. Czaniik and S. H. DeWitt, *Practical Guide to Combinatorial Chemistry*, ACS, Washington, D.C. (1997)). The LEGION and SELECTOR modules are said to be useful in creating libraries and characterizing molecules in terms of both 2-dimensional and 3-dimensional structural fingerprints, substituent parameters, topological indices, and physicochemical parameters.

Preclinical evaluation of lead compounds in animals is a critical step for successful drug discovery. For cancer therapeutics, two types of mouse models provide easy and reliable initial preclinical testing of lead compounds: a) a mouse xenograft model, in which foreign (e.g., human) tumors are implanted into immune deficient mice, where they implant and grow and where their response in vivo to lead compounds can be measured; and b) a genetic tumor mouse model, in which the mouse is bred to have a genetic deficiency that results in the development of a tumor at a certain age. The latter is a more predictive model of drug success in humans, but the former afford the capability to test the efficacy of drugs designed to target human proteins inside the mouse. For the unfolded protein response, the Tsc +/−mouse model is an appropriate genetic model (Ozcan U, et al., "Loss of the Tuberous Sclerosis Complex Tumor Suppressors Triggers the Unfolded Protein Response to Regulate Insulin Signaling and Apoptosis," *Mol. Cell;* 29:541-551 (2008)) and several standard xenograft models are available (Bi M, et al., "ER Stress-regulated Translation Increases Tolerance to Extreme Hypoxia and Promotes Tumor Growth," *EMBO J;* 24:3470-81 (2002)). The SXFAD mouse transgenic model is an appropriate animal model for the preclinical evaluation of lead compounds on their pharmacologic inhibition of Alzheimer's disease progression. Pursuing a model of mouse PERK inhibition first and then translating the findings to human PERK via xenograft models represents a more feasible pathway of preclinical mouse testing of lead compounds.

The present invention is directed to overcoming these and other deficiencies in the art.

SUMMARY OF THE INVENTION

In one aspect, the present invention relates to a method of identifying compounds useful in inhibiting protein kinase-like endoplasmic reticulum protein kinase (PERK). This method involves providing a first model comprising PERK active domain(s), the active domain(s) being selected from the group consisting of the peptide spanning from amino acid residue Asp144 to the amino acid residue Ser191 of SEQ ID NO: 1 and peptides comprising the amino acid residue at position 7 of SEQ ID NO: 1, providing one or more candidate compounds, evaluating contact between the candidate compounds and the first model to determine which of the one or more candidate compounds have an ability to bind to and/or fit in the first model, and identifying the compounds which, based on the evaluating, have the ability to bind to and/or fit in the first model as compounds potentially useful for inhibiting PERK.

In another aspect, the present invention relates to a method of treating a PERK-mediated condition in a subject. This method comprises selecting a subject with the PERK-mediated condition, providing a compound which binds to and/or fits in a model comprising the PERK active domain, where the active domain is selected from the group consisting of the peptide spanning from amino acid residue Asp144 to amino acid residue Ser191 of SEQ ID NO: 1 and peptides comprising the amino acid residue at position 7 of SEQ ID NO: 1, and administering the compound to the selected subject under conditions effective to treat the PERK-mediated condition in the subject.

In yet another aspect the present invention relates to a pharmaceutical composition comprising a compound selected from the group consisting of:

(1) a compound of formula (I):

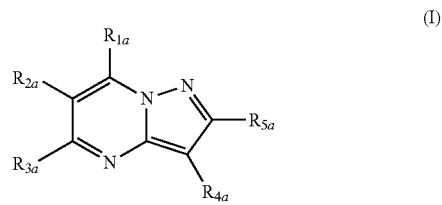

wherein:
R$_{1a}$ is independently H, halogen, CF$_3$, CHF$_2$, CH$_2$F, OR$_{6a}$, C$_1$-C$_6$ alkyl, C$_2$-C$_6$ alkenyl, C$_2$-C$_6$ alkynyl, C$_1$-C$_6$ alkoxy, C$_3$-C$_6$ cycloalkyl, C$_4$-C$_7$ cycloalkylalkyl, aryl C$_1$-C$_6$ alkyl, mono or polycyclic aryl, or mono or polycyclic heteroaryl containing from 1 to 5 heteroatoms selected from the group consisting of nitrogen, sulfur, and oxygen;

$R_{2a}$ and $R_{4a}$ are independently H, halogen, $C_1$-$C_6$ alkyl, $C_2$-$C_6$ alkenyl, or $C_2$-$C_6$ alkynyl;

$R_{3a}$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of $R_{3a}$ optionally substituted from 1 to 4 times for each cyclic ring with substituents selected from the group consisting of H, $OR_{6a}$, —C(O)$R_{6a}$, —C(O)O$R_{6a}$, —C(O)NR$_{6a}$R$_{7a}$, —NHR$_{6a}$, —NR$_{6a}$R$_{7a}$, —SR$_{6a}$, —S(O)R$_{6a}$, —S(O)$_2$R$_{6a}$, NH$_2$, CN, NO$_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl;

$R_{5a}$ is independently H, —C(O)$R_{6a}$, —C(O)O$R_{6a}$, —C(O)NR$_{6a}$R$_{7a}$, —S(O)R$_{6a}$, or —S(O)$_2$R$_{7a}$;

$R_{6a}$ is independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen; and $R_{7a}$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of $R_{7a}$ optionally substituted from 1 to 4 times for each cyclic ring with substituents selected from the group consisting of H, OH, $OR_{6a}$, —C(O)$R_{6a}$, —C(O)O$R_{6a}$, —C(O)NR$_{6a}$R$_{7a}$, —NHR$_{6a}$, —NR$_{6a}$R$_{7a}$, —SR$_{6a}$, —S(O)R$_{6a}$, —S(O)$_2$R$_{6a}$, NH$_2$, CN, NO$_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl;

(2) a compound of formula (II):

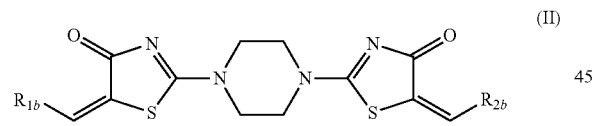

(II)

wherein:

$R_{1b}$ and $R_{2b}$ are independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of $R_{1b}$ or $R_{2b}$ optionally substituted from 1 to 4 times for each cyclic ring with substituents selected from the group consisting of H, OH, $OR_{3b}$, —C(O)$R_{3b}$, —C(O)O$R_{3b}$, —C(O)NR$_{3b}$R$_{4b}$, —NHR$_{3b}$, —NR$_{3b}$R$_{4b}$, —SR$_{3b}$, —S(O)R$_{3b}$, —S(O)$_2$R$_{3b}$, NH$_2$, CN, NO$_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl; and $R_{3b}$ and $R_{4b}$ are independently $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen;

(3) a compound of formula (III):

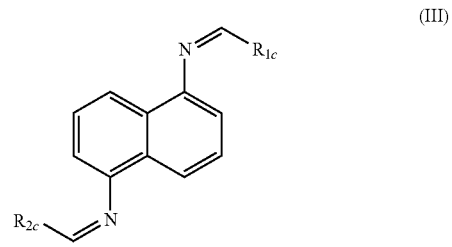

(III)

wherein:

$R_{1c}$ and $R_{2c}$ are independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of $R_{1c}$ and $R_{2c}$ optionally substituted from 1 to 4 times for each cyclic ring with substituents selected from the group consisting of H, OH, $OR_{3c}$, —C(O)$R_{3c}$, $R_{3c}$C(O)O—, —C(O)NR$_{3c}$R$_{4c}$, —NHR$_{3c}$, —NR$_{3c}$R$_{4c}$, —SR$_{3c}$, —S(O)R$_{3c}$, —S(O)$_2$R$_{3c}$, NH$_2$, CN, NO$_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl; and $R_{3c}$ and $R_{4c}$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen;

(4) a compound of formula (IV):

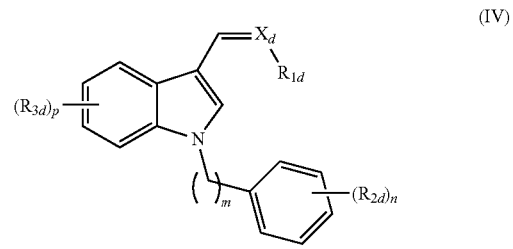

(IV)

wherein:

$X_d$ is N or $CR_{4d}R_{5d}$;

m, n, or p are integers from 0 to 5;

$R_{1d}$ is independently H or $R_{6d}$C(O)N($R_{7d}$)—;

$R_{2d}$ and $R_{3d}$ are independently H, halogen, $OR_{4d}$, $C_1$-$C_6$ alkyl, $C_2$-$C_6$ alkenyl, or $C_2$-$C_6$ alkynyl;

$R_{4d}$ and $R_{5d}$ are combined to form a substituted or unsubstituted mono or polycyclic heteroaryl containing from 1 to 5 heteroatoms selected from the group consisting of oxygen, nitrogen, and sulfur, each mono or polycyclic heteroaryl optionally substituted from 1 to 4 times for each cyclic ring with substituents selected from the group consisting of H, OH, NH$_2$, CN, NO$_2$, halogen, oxo, thio, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl; and $R_{6d}$ and $R_{7d}$ are independently H, $C_1$-$C_6$ alkyl, $C_2$-$C_6$ alkenyl, $C_2$-$C_6$ alkynyl, a substituted or unsubstituted mono or polycyclic heteroaryl containing from 1 to 5 heteroatoms selected from the group consisting of oxygen, nitrogen, and sulfur, each one of $R_{6d}$ and $R_{7d}$ optionally substituted from 1 to 3 times with substituents selected from the group consisting of OH, $NH_2$, CN, $NO_2$, halogen, oxo, thio, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl;

(5) a compound of formula (V):

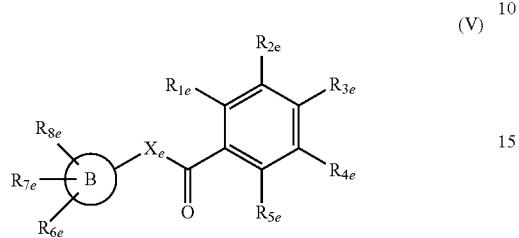

(V)

wherein:

B represents a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of B optionally substituted from 1 to 4 times for each cyclic ring with substituents selected from the group consisting of OH, $NH_2$, CN, $NO_2$, halogen, oxo, thio, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl;

$X_e$ represents O or $NR_{9e}$;

$R_{1e}$, $R_{2e}$, $R_{3e}$, $R_{4e}$, and $R_{5e}$ are independently H, halogen, $OR_{9e}$, $R_{9e}C(O)NH$—, $C_1$-$C_6$ alkyl, $C_2$-$C_6$ alkenyl, or $C_2$-$C_6$ alkynyl;

$R_{6e}$, $R_{7e}$, and $R_{8e}$ are independently H, halogen, OH, $NH_2$, —$CR_{9e}$=$NR_{10e}$, arylalkyl, $C_1$-$C_6$ alkyl, $C_2$-$C_6$ alkenyl, $C_2$-$C_6$ alkynyl, a substituted or unsubstituted mono or polycyclic heteroaryl containing from 1 to 5 heteroatoms selected from the group consisting of oxygen, nitrogen, and sulfur, each one of $R_{6e}$, $R_{7e}$, or $R_{8e}$ optionally substituted from 1 to 3 times with substituents selected from the group consisting of OH, $NH_2$, CN, $NO_2$, halogen, $C_1$-$C_6$ alkyl, $C_1$-$C_6$ alkoxy, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl;

$R_{9e}$ is independently H, $C_1$-$C_6$ alkyl, $C_2$-$C_6$ alkenyl, $C_2$-$C_6$ alkynyl, a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of $R_{9e}$ optionally substituted from 1 to 3 times with substituents selected from the group consisting of OH, $NH_2$, CN, $NO_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl;

$R_{10e}$ is independently H or $R_{12e}C(O)NR_{13e}$—; and $R_{12e}$ and $R_{13e}$ are independently H, $C_1$-$C_6$ alkyl, $C_2$-$C_6$ alkenyl, or $C_2$-$C_6$ alkynyl, each one of $R_{12e}$ and $R_{13e}$ optionally substituted from 1 to 4 times with substituents selected from the group consisting of OH, $OR_{9e}$, $NH_2$, CN, $NO_2$, halogen, oxo, thio, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl; and (6) a compound of formula (VI):

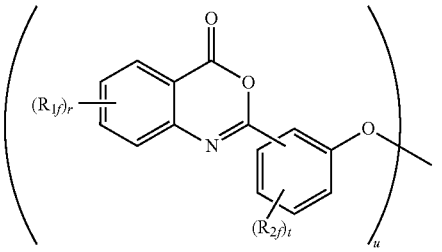

(VI)

wherein:

u is an integer 2 or 4;

r and t are integers from 1 to 4; and $R_{1f}$ and $R_{2f}$ are independently H, halogen, $NO_2$, CN, $C_1$-$C_6$ alkoxy, $C_1$-$C_6$ alkyl, $C_2$-$C_6$ alkenyl, or $C_2$-$C_6$ alkynyl.

The essential role of PERK in tumor survival and growth has been established by the observation that tumors that lack PERK activity were relatively small and exhibit a diminished capability to translate mRNAs involved in angiogenesis, tumor survival and growth. This suggests that compromising PERK function may inhibit tumor growth via lower phosphorylation of eIF2α. The role of PERK in Alzheimer's disease (AD) is supported by autopsy studies showing hyperactive PERK and its substrate eIF2α in neurons of AD patients and the observation that PERK inhibition blocks BACE1, an enzyme that induces AD pathogenesis, increase through eIF2α phosphorylation. Beta-site APP cleaving enzyme-1 (BACE-1), the rate-limiting enzyme for beta-amyloid production is elevated in Alzheimer's disease (O'Connor et al., "Phosphorylation of the Translation Initiation Factor eIF2α Increases BACE1 Levels and Promotes Amyloidogenesis," Neuron 60, 988-1009 (2008), which is hereby incorporated by reference in its entirety) Inhibiting the kinase activity of PERK towards eIF2α is thus an important and novel target for therapeutic intervention in cancer and Alzheimer's disease. To date, however, no specific small molecule inhibitor of PERK has been identified. The present invention identifies the important receptor-ligand atomic contacts responsible for selective mouse PERK inhibition, and proposes that the equivalent human contacts can be similarly utilized. For this purpose, two homology models of mouse PERK catalytic domain were constructed. Subsequently, structure-based virtual library screening (VLS) and chemoinformatic tools were utilized, in conjunction with in vitro kinase inhibition assay, to identify the structural determinants of PERK inhibitor activity, selectivity and potency.

The present invention describes the first pharmacophore model for selective inhibitors of PERK. Structural features of the pharmacophore model for selective PERK inhibitors can be used for the development of more potent and selective PERK inhibitors through structure-based PERK inhibitor design. Specifically, a strong van der Waals contact with amino acid residue 7 of SEQ ID NO: 1, interactions with the N-terminal portion of the activation loop, and electrostatic complementarity to Asp-144 are three important structural determinants of PERK inhibition by a small molecule compound.

BRIEF DESCRIPTION OF THE DRAWINGS

FIG. 1A illustrates the predicted binding mode of two active compounds A4 and D1 showing strong Met-7 van der Waals contact. The receptor is shown in ribbon representation. The surface of the binding site is displayed as a mesh colored according to binding properties: green stands for hydrophobic; blue stands for hydrogen bond donor; red stands for hydrogen bond acceptor. Hydrogen bonds are depicted as a row of small balls. Met-7 is represented as space-filling solid model. FIG. 1B shows the generation of corresponding compounds with no Met-7 contact for the active compounds A4 and D1. The highlighted chemical groups were the substructure search queries. FIG. 1C shows the inhibition of PERK-dependent eIF2α phosphorylation in vitro for compound A4 and D1. Lane 1: no compound added; lanes 2-6: different compounds tested at a concentration of 10 µM. Arrows indicate active compounds A4 (lane 2) and D1 (lane 4). Lanes 3, 5, and 6 are the compounds which tested inactive. FIG. 1D shows in vitro test on the corresponding compounds with no Met-7 contact for A4 and D1. Compounds were tested at a concentration of 40 µM. Lane 1: no compound added; lane 2: compound D1; lanes 3-4: the corresponding compounds with no Met-7 contact for A4 and D1, respectively. FIG. 1E shows in vitro test for PKA inhibition on the six active compounds in the initial virtual library screening (VLS) showing Met-7 is a structural determinant to distinguish between the active and inactive compounds, but is not itself a determinant of selectivity for PERK. Equivalently, the amino acid present at this structural location in human PERK, regardless of whether it is Met or another amino acid, may be viewed as a structural determinant to distinguish between active and inactive compounds against human PERK. Lane 1: no compound added; lanes 2-7: compounds tested at a concentration of 25 µM.

FIG. 2A shows that A4 makes hydrogen bonds with two residues in the activation loop. FIG. 2B shows that D1 makes hydrogen bonds with two residues in the hinge region. The receptors are shown as ribbon. The residues making hydrogen bonds with the inhibitors are displayed as wire. Hydrogen bonds are depicted as a row of small balls.

FIG. 3A shows the inhibition of PERK-dependent eIF2α phosphorylation in vitro by the nine compounds making extensive contacts with the activation loop area. Lane 1: no compound added; lane 2: compound A4 as a positive control; lanes 3-11: nine compounds tested at a concentration of 40 µM. FIG. 3B shows in vitro test of PKA inhibition on the nine compounds. Lane 1: no compound added; lane 2: a non-selective compound as the control; lanes 3-11: nine compounds tested at a concentration of 40 µM. FIG. 3C shows the predicted binding mode of a selective compound showing extensive contacts with the activation loop area. This compound corresponds to lane 9 in FIGS. 3A and 3B. The receptors are shown as ribbon. The residues making contact with the inhibitors are displayed as wire.

FIG. 4A shows that the partial positive charge in A4B2, an active compound with an $IC_{50}$ of 1 µM, has electrostatic complementarity to the negative charge of the oxygen in Asp-144 side chain. FIG. 4B shows the partial negative charge in A4B5, an active compound with an $IC_{50}$ of 30 µM, shows electrostatic repulsion to the negative charge in Asp-144 side chain. FIG. 4C shows the in vitro test on the compounds repulsive to the oxygen in Asp-144 side chain, corresponding to the active compounds with an $IC_{50}$ lower than 10 µM. Compounds were tested at a concentration of 40 µM. Lane 1: no compound added; lane 2: an active compound as a positive control; lanes 3-9: the corresponding compounds repulsive to the oxygen in Asp-144 side chain.

FIG. 7 shows a sequence alignment of SEQ ID NO: 1, SEQ ID NO: 2, and SEQ ID NO: 3.

FIG. 8 shows the sequence alignment of SEQ ID NO: 3 and SEQ ID NO: 4.

DETAILED DESCRIPTION OF THE INVENTION

Figure 1:
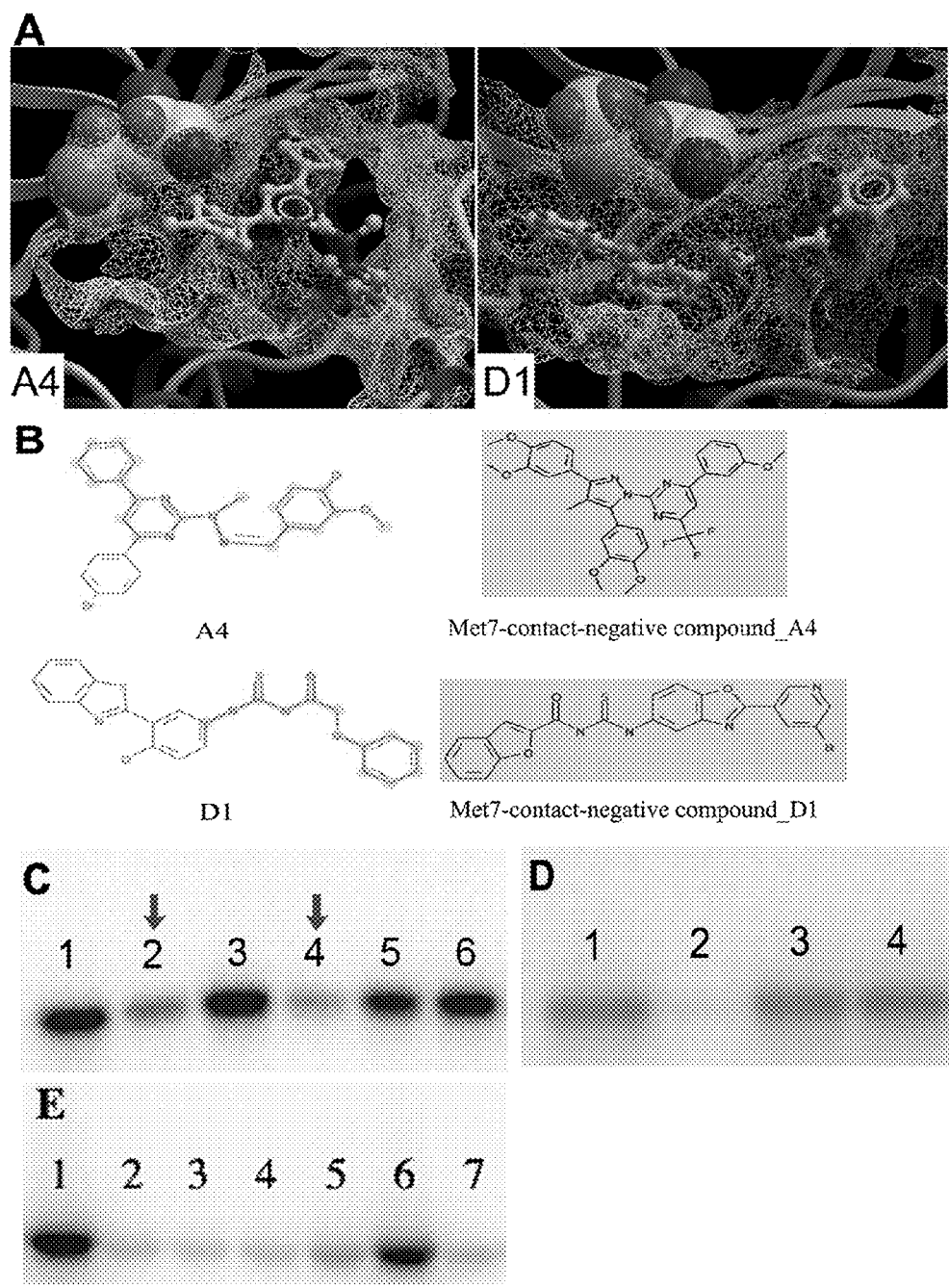
FIGS. 1A-E show that strong van der Waals contacts with Methionine-7 (Met-7) is a structural determinant for compound activity.

In one aspect, the present invention relates to a method of identifying compounds useful in inhibiting protein kinase-like endoplasmic reticulum protein kinase (PERK). This method involves providing a first model comprising PERK active domain(s), the active domain(s) being selected from the group consisting of the peptide spanning from amino acid residue Asp144 to the amino acid residue Ser191 of SEQ ID NO: 1 and peptides comprising the amino acid residue at position 7 of SEQ ID NO: 1, providing one or more candidate compounds, evaluating contact between the candidate compounds and the first model to determine which of the one or more candidate compounds have an ability to bind to and/or fit in the first model, and identifying the compounds which, based on the evaluating, have the ability to bind to and/or fit in the first model as compounds potentially useful for inhibiting PERK.

In one embodiment the first model comprises the peptide spanning from amino acid residue Asp144 to the amino acid residue Ser191 of SEQ ID NO: 1. In another embodiment the first model comprises the peptides comprising the amino acid residue at position 7 of SEQ ID NO: 1.

The amino acid sequence of SEQ ID NO: 1 is as follows:

```
  1 FEPIQCXGRG GFGVVFEAKN KVDDCNYAIK RIRLPNRELA REKVMREVKA

51 LAKLEHPGIV RYFNAWLEXK VYLYIQMQLC RKENLKDWMN XRCXXEXREX

101 XVCLHIFLQI AEAVEFLHSK GLMHRDLKPS NIFFTMDDVV KVGDFGLVTA

151 MDQDEEEQTV LTPMPAYAXH TGQVGTKLYM SPEQIHGNXY SHKVDIFSLG

201 LILFELLYPF STXMERVRXL TDVRNLKFPX LFTQKYPXEX XMVQDMLSPS

251 PXERPEAXXI IENAXFEXLX FPGKTVLR
```

$X_7$ is M, L;
$X_{69}$ is A, T;
$X_{91}$ is G, R;
$X_{94}$ is S, T;
$X_{95}$ is I, L;
$X_{97}$ is E, D;
$X_{100}$ is R, H;
$X_{101}$ is S, G;
$X_{169}$ is R, T;
$X_{189}$ is S, N;
$X_{213}$ is Q, L;
$X_{219}$ is T, I;
$X_{230}$ is P, L;
$X_{238}$ is Q, C;
$X_{240}$ is Y, H;
$X_{241}$ is V, M;
$X_{252}$ is M, T;
$X_{258}$ is I, T;
$X_{259}$ is N, D;
$X_{265}$ is V, I;
$X_{268}$ is D, N;
$X_{270}$ is D, E.

The subscripts in residues $X_7$, $X_{69}$, $X_{91}$, $X_{94}$, $X_{95}$, $X_{97}$, $X_{100}$, $X_{101}$, $X_{169}$, $X_{189}$, $X_{213}$, $X_{219}$, $X_{230}$, $X_{238}$, $X_{240}$, $X_{241}$, $X_{252}$, $X_{258}$, $X_{259}$, $X_{265}$, $X_{268}$, and $X_{270}$ refer to the amino acid residue position in SEQ ID NO: 1.

The amino acid sequence of the catalytic domain of the mouse PKR-like endoplasmic reticulum protein kinase (PERK) (SEQ ID NO: 2) used to build the 3D structural model that was used to identify compounds is as follows:

```
  1 FEPIQCMGRG GFGVVFEAKN KVDDCNYAIK RIRLPNRELA REKVMREVKA

51 LAKLEHPGIV RYFNAWLETK VYLYIQMQLC RKENLKDWMN RRCSLEDREH

101 GVCLHIFLQI AEAVEFLHSK GLMHRDLKPS NIFFTMDDVV KVGDFGLVTA

151 MDQDEEEQTV LTPMPAYATH TGQVGTKLYM SPEQIHGNNY SHKVDIFSLG

201 LILFELLYPF STLMERVRIL TDVRNLKFPL LFTQKYPQEH MMVQDMLSPS

251 PTERPEATDI IENAIFENLE FPGKTVLR
```

This catalytic domain is composed of two discontinuous segments from whole mouse PERK (GenBank ID AAD03337) that in the three-dimensional structure from a single compact folded domain with intrinsic kinase activity. The intervening segment between the two discontinuous segments is a domain called the "delta loop", which is unimportant to the kinase activity of the catalytic domain of PERK and of unknown structure and is inserted into the N-terminal lobe of the catalytic domain of PERK beginning after residue 70 in SEQ ID NO: 2.

The amino acid sequence of whole mouse PERK (Gen-Bank ID AAD03337), including this catalytic domain, the intervening N-terminal lobe domain and additional domains before and after the catalytic domain in the sequence is (SEQ ID NO: 3):

```
  1 MERATRPGPR ALLLLLFLLL GCAAGISAVA PARSLLAPAS ETVFGLGAAA

51 APTSAARVPA VATAEVTVED AEALPAAAGE PESRATEPDD DVELRPRGRS

101 LVIISTLDGR IAALDAENDG KKQWDLDVGS GSLVSSSLSK PEVFGNKMII

151 PSLDGDLFQW DRDRESMEAV PFTVESLLES SYKFGDDVVL VGGKSLITYG

201 LSAYSGKLRY ICSALGCRRW DSDEMEEEED ILLLQRTQKT VRAVGPRSGS

251 EKWNFSVGHF ELRYIPDMET RAGFIESTFK PGGNKEDSKI ISDVEEQEAT
```

```
301  MLDTVIKVSV ADWKVMAFSR KGGRLEWEYQ FCTPIASAWL VRDGKVIPIS
351  LFDDTSYTAS EEALGDEEDI VEAARGATEN SVYLGMYRGQ LYLQSSVRVS
401  EKFPTSPKAL ESVNGENAII PLPTIKWKPL IHSPSRTPVL VGSDEFDKCL
451  SNDKYSHEEY SNGALSILQY PYDNGYYLPY YKRERNKRST QITVRFLDSP
501  HYSKNIRKKD PILLLHWWKE IFGTILLCIV ATTFIVRRLF HPQPHRQRKE
551  SETQCQTESK YDSVSADVSD NSWNDMKYSG YVSRYLTDFE PIQCMGRGGF
601  GVVFEAKNKV DDCNYAIKRI RLPNRELARE KVMREVKALA KLEHPGIVRY
651  FNAWLETPPE KWQEEMDEIW LKDESTDWPL SSPSPMDAPS VKIRRMDPFS
701  TKEQIEVIAP SPERSRSFSV GISCGQTSSS ESQFSPLEFS GTDCGDNSDS
751  ADAAYNLQDS CLTDCEDVED GTVDGNDEGH SFELCPSEAS PYTRSREGTS
801  SSIVFEDSGC GNASSKEEPR GNRLHDGNHY VNKLTDLKCS SSRSSSEATT
851  LSTSPTRPTT LSLDFTKNTV GQLQPSSPKV YLYIQMQLCR KENLKDWMNR
901  RCSLEDREHG VCLHIFLQIA EAVEFLHSKG LMHRDLKPSN IFFTMDDVVK
951  VGDFGLVTAM DQDEEEQTVL TPMPAYATHT GQVGTKLYMS PEQIHGNNYS
1001 HKVDIFSLGL ILFELLYPFS TQMERVRILT DVRNLKFPLL FTQKYPQEHM
1051 MVQDMLSPSP TERPEATDII ENAIFENLEF PGKTVLRQRS RSMSSSGTKH
1101 SRQPSCSYSP LPGN
```

The amino acid sequence of whole human eukaryotic translation initiation factor 2α kinase PEK (GenBank ID AAF61199.1) (SEQ ID NO: 4), including the catalytic domain, the intervening N-terminal lobe domain and additional domains before and after the catalytic domain in the sequence is as follows:

```
   1 MERAISPGLL VRALLLLLLL GLAARTVAAG RARGLPAPTA EAAFGLGAAA
  51 APTSATRVPA AGAVAAAEVT VEDAEALPAA AGEQEPRGPE PDDETELRPR
 101 GRSLVIISTL DGRIAALDPE NHGKKQWDLD VGSGSLVSSS LSKPEVFGNK
 151 MIIPSLDGAL FQWDRDRESM ETVPFTVESL LESSYKFGDD VVLVGGKSLT
 201 TYGLSAYSGK VRYICSALGC RQWDSDEMEQ EEDILLLQRT QKTVRAVGPR
 251 SGNEKWNFSV GHFELRYIPD METRAGFIES TFKPNENTEE SKIISDVEEQ
 301 EAAIMDIVIK VSVADWKVMA FSKKGGHLEW EYQFCTPIAS AWLLKDGKVI
 351 PISLFDDTSY TSNDDVLEDE EDIVEAARGA TENSVYLGMY RGQLYLQSSV
 401 RISEKFPSSP KALESVTNEN AIIPLPTIKW KPLIHSPSRT PVLVGSDEFD
 451 KCLSNDKFSH EEYSNGALSI LQYPYDNGYY LPYYKRERHK RSTQITVRFL
 501 DNPHYNKNIR KKDPVLLLHW WKEIVATILF CIIATTFIVR RLFHPHPHRQ
 551 RKESETQCQT ENKYDSVSGE ANDSSWNDIK NSGYISRYLT DFEPIQCLGR
 601 GGFGVVFEAK NKVDDCNYAI KRIRLPNREL AREKVMREVK ALAKLEHPGI
 651 VRYFNAWLEA PPEKWQEKMD EIWLKDESTD WPLSSPSPMD APSVKIRRMD
 701 PFSTKEHIEI IAPSPQRSRS FSVGISCDQT SSSESQFSPL EFSGMDHEDI
 751 SESVDAAYNL QDSCLTDCDV EDGTMDGNDE GHSFELCPSE ASPYVRSRER
 801 TSSSIVFEDS GCDNASSKEE PKTNRLHIGN HCANKLTAFK PTSSKSSSEA
 851 TLSISPPRPT TLSLDLTKNT TEKLQPSSPK VYLYIQMQLC RKENLKDWMN
 901 GRCTIEERER SVCLHIFLQI AEAVEFLHSK GLMHRDLKPS NIFFTMDDVV
 951 KVGDFGLVTA MDQDEEEQTV LTPMPAYARH TGQVGTKLYM SPEQIHGNSY
```

```
-continued
1001  SHKVDIFSLG LILFELLYPF STQMERVRTL TDVRNLKFPP LFTQKYPCEY

1051  VMVQDMLSPS PMERPEAINI IENAVFEDLD FPGKTVLRQR SRSLSSSGTK

1101  HSRQSNNSHS PLPSN
```

FIG. 7 shows the sequence alignment of SEQ ID NO: 1, SEQ ID NO: 2, and SEQ ID NO: 3. FIG. 8 shows the sequence alignment of SEQ ID NO: 3 and SEQ ID NO: 4.

In one embodiment of this aspect of the present invention, the method further comprises providing a second model comprising a peptide comprising amino acid residue Aspartate-144 of SEQ ID NO: 1 (equivalent to Asp144 in SEQ ID NO: 2 and to Asp953 in SEQ ID NO: 3). Contact between the identified candidate compounds and the second model is examined to determine which of the identified candidate compounds have the ability to bind to and/or fit in the second model. The identified compounds which, based on said examining, have the ability to bind to and/or fit in the second model are designated as compounds with enhanced potential to inhibit PERK.

In another embodiment of the present invention, the binding to/fitting in the second model by the compound(s) involves interactions such as electrostatic complementarity.

When the first model comprises the amino acid residue 7 of SEQ ID NO: 1, the binding to/fitting in the residue 7 by the compound(s) involves interactions due to van der Waals forces.

Providing a Model of PERK and its Fragments

Scientists in this field will appreciate that whole PERK molecule or its domains or fragments could be used for model building and for the purposes of the present invention. Relevant domains or fragments of PERK comprise residues such as amino acid residue 7, Asp-144 of SEQ ID NO: 1 or Met-7, Asp-144 of SEQ ID NO: 2 which are identified as relevant for design of compounds that may inhibit the function of PERK. Once an appropriate model is obtained, domains or fragments of this model can be obtained by, for example, modifying the atomic coordinates of the model to provide atomic coordinates for domains or fragments or by selectively defining the relevant domains of the model in an input file that is to be used for computational calculations.

As is well known in the art, there are many ways available to provide a model for a protein or other macromolecule. As the art improves, much more sophisticated methods might become available for use in modeling the structure of molecules of the present invention. The description provided below is intended to provide non limiting examples of methods which can be used for providing a model for PERK and/or its domains or fragments. Typically experimental techniques such as X-ray crystallography (Clegg W, *Crystal Structure Determination* (*Oxford Chemistry Primer*), Oxford: Oxford University Press (1998); Drenth J, *Principles of Protein X-Ray Crystallography*, New York: Springer-Verlag (1999), which are hereby incorporated by reference in their entirety) or Nuclear Magnetic Resonance (NMR) (T. Kevin Hitchens, *Fundamentals of Protein NMR Spectroscopy* (*Focus on Structural Biology*), Berlin: Springer (2005); Quincy Teng, *Structural Biology: Practical NMR Applications*, Berlin: Springer (2005), which are hereby incorporated by reference in their entirety) could be used to generate a model for PERK or its fragments. These two experimental techniques can provide high resolution structures of macromolecules.

Optionally molecular modeling techniques may also be used to generate models of PERK and its domains. Molecular modeling can also be used for protein structure prediction of PERK or its fragments. Molecular modeling approaches to protein structure prediction are of importance in medicine (for example, in drug design) and biotechnology (for example, in the design of novel enzymes). The ultimate goal of protein structure prediction, in general, is the prediction of the three-dimensional structure of a protein from just its amino acid sequence.

Molecular modeling can be used generate one or more 3D models of a structural feature of a macromolecule, for example, a ligand binding site, a catalytic site. Molecular modeling techniques can be performed manually, with the aid of a computer, or with a combination of these. For example, molecular modeling techniques can be applied to generate the atomic co-ordinates of PERK to derive a range of 3D models and to investigate the structure of active/catalytic site of PERK.

Molecular modeling approaches to protein structure prediction can be broadly divided in to two categories: comparative modeling and ab initio-modeling. In both cases, an energy function is needed to recognize the native structure, and to guide the search for the native structure. In a comparative structure prediction approach to molecular modeling (also called homology modeling), the search space is pruned by the assumption that the protein in question adopts a structure that is reasonably close to the structure of at least one known protein. Comparative protein modeling uses previously solved structures as starting points, or templates. This is effective because it appears that although the number of actual proteins is vast, there is a limited set of tertiary structural motifs to which most proteins belong. These comparative methods can also be split into two groups: Homology based modeling and protein threading.

Homology modeling is based on the reasonable assumption that two homologous proteins will share very similar structures. Because a protein's fold is more evolutionarily conserved than its amino acid sequence, a target sequence can be modeled with reasonable accuracy on a very distantly related template, provided that the relationship between target and template can be discerned through sequence alignment. It has been suggested that the primary bottleneck in comparative modeling arises from difficulties in alignment rather than from errors in structure prediction given a known-good alignment (Zhang et al., "Progress and Challenges in Protein Structure Prediction," *Curr Opin Struct Biol* 18: 342-348 (2008), which is hereby incorporated by reference in its entirety). Unsurprisingly, homology modeling is most accurate when the target and template have similar sequences.

Protein threading (Bowie et al., "A Method to Identify Protein Sequences that Fold into a Known Three-dimensional Structure," *Science* 253: 164-170(1991), which is hereby incorporated by reference in its entirety) scans the amino acid sequence of an unknown structure against a database of solved structures. In each case, a scoring function is used to assess the compatibility of the sequence to the structure, thus yielding possible three-dimensional models. This type of method is also known as 3D-1D fold recognition due to its compatibility analysis between three-dimensional structures and linear protein sequences. This method has also given rise to methods performing an inverse folding search by evaluating the compatibility of a given structure with a large database of sequences, thus predicting which sequences have the potential to produce a given fold.

In de novo or ab initio structure prediction, no assumption of structural similarity between two homologous proteins is made, which results in a much harder search problem. Ab initio- or de-novo-protein modeling methods seek to build three-dimensional protein models "from scratch", i.e., based on physical principles rather than (directly) on previously solved structures. There are many possible procedures that either attempt to mimic protein folding or apply some stochastic method to search possible solutions (i.e., global optimization of a suitable energy function). These procedures tend to require vast computational resources.

In the case of complexes involving two or more proteins, where the structures of the proteins are known or can be predicted with high accuracy, protein-protein docking methods can also be used to predict the structure of the complex. Information of the effect of mutations at specific sites on the affinity of the complex helps to understand the complex structure and to guide docking methods.

Many software tools are available for molecular modeling. For example, MODELLER is a popular software tool for producing homology models using methodology derived from NMR spectroscopy data processing. SwissModel provides an automated web server for basic homology modeling. I-TASSER is a server for protein structure prediction according to the recent CASP experiments (CASP7 and CASP8). Common software tools for protein threading are HHpred/HHsearch, Robetta, and Phyre. RAPTOR is a protein threading software that is based on integer programming. The basic algorithm for threading is described in Bowie et al., "A Method to Identify Protein Sequences that Fold into a Known Three-dimensional Structure," *Science* 253: 164-170 (1991), which is hereby incorporated by reference in its entirety, and is fairly straightforward to implement. Abalone is a Molecular Dynamics program for folding simulations with explicit or implicit water models.

Typical suites of software include CERIUS$^2$ (Accelrys, San Diego, Calif.), SYBYL (Tripos Inc., St. Louis, Mo.), AMBER (University of California, San Francisco), HYPERCHEM (Hypercube Inc., Gainesville, Fla.), INSIGHT II (Accelrys, San Diego, Calif.), CATALYST (Accelrys, San Diego, Calif.), CHEMSITE (ChemSW, Fairfield, Calif.), QUANTA (Accelrys, San Diego, Calif.). These packages implement many different algorithms that may be used according to the present invention (e.g. CHARMM molecular mechanics (Brooks et al., "CHARMM: A Program for Macromolecular Energy, Minimization, and Dynamics Calculations," *J. Comp. Chem.* 4,187-217 (1983), which is hereby incorporated by reference in its entirety). Their uses in the methods of the present invention include, but are not limited to: (a) interactive modeling of the structure with concurrent geometry optimization (e.g. QUANTA); (b) molecular dynamics simulation of PERK or its domains (e.g. CHARMM, AMBER); (c) normal mode dynamics simulation of PERK or its domains (e.g. CHARMM). Modeling may include one or more steps of energy minimization with standard molecular mechanics force fields, such as those used in CHARMM and AMBER. These molecular modeling softwares usually allow the construction of structural models that can be further used for de-novo drug design or for combinatorial approaches towards drug design.

Further reviews of software for structure prediction can be found in Nayeem et al., "A Comparative Study of Available Software for High-accuracy Homology Modeling: From Sequence Alignments to Structural Models," *Protein Sci* 15: 808-824 (2006), which is hereby incorporated by reference in its entirety. The progress and challenges in protein structure prediction has been reviewed by Zhang et al., "Progress and Challenges in Protein Structure Prediction," *Curr Opin Struct Biol* 18: 342-348 (2008), which is hereby incorporated by reference in its entirety.

Selection of Candidate Compounds

The methods of the present invention comprise selecting one or more candidate compounds. This can be done by many methods known in the art. The most important issue when selecting the candidate compounds is to be able to identify key molecular features of the candidate compound and the target which make binding between the compound and the candidate possible. The process of selecting candidate compounds may involve various steps such as the identification of candidates, synthesis, characterization, screening, and assays for therapeutic efficacy.

Among the most important advances in drug development have been advances in combinatorial synthesis of chemical libraries. In conventional drug screening with purified enzyme targets, combinatorial chemistries can often help create new derivatives of a lead compound that will also inhibit the target enzyme but with some different and desirable property. Well designed chemical libraries are an essential part of drug design. The present invention could be practiced by either screening for drug compounds and/or by de novo design of drug compounds against the PERK molecules or relevant fragments. There is such large chemical space available for drug-candidate molecules that conducting an effective search has been difficult in the past. Drug candidates can be identified using de-novo design, which can be helpful in producing novel molecular structures with desired pharmacological properties and also in narrowing down the chemical search space. It provides a substitute for a systematic construction and evaluation of individual compounds and relies on some kind of structure optimization algorithm, described below, where an optimization of the interactions between the candidate drug and the target is carried out. Often the aim is to incorporate as much chemical knowledge as possible about the structure of the target and the candidate drug into the search or design algorithms to restrict the search space and therefore facilitate the directed navigation to the drug which interacts effectively with the target.

Screening of candidate compounds and chemical libraries can be done by various methods known the art. High throughput screening is a method of drug discovery that involves a brute force approach where tens of thousands of compounds are tested against a particular target. Compound libraries can have millions of compounds, selected for drug-like characteristics such as solubility, partition coefficient (log P), molecular weight, and number of hydrogen bond donors/acceptors. Generally, high throughput screening involves modern robotics, sophisticated control software, advanced liquid handling, and sensitive detection methods. The hits generated during HTS can be used as the starting point for a drug discovery effort. Typically, hits are refined through medicinal chemistry and lower-throughput assays. High throughput assays can be classified as either functional or nonfunctional. Functional assays measure the activity of a compound in modifying the actual function of a target protein (e.g., ion currents through hERG channels). Nonfunctional assays often simply measure binding of a compound to the target protein or use some indirect measure of target activity. Examples of nonfunctional assays include tritiated binding assays, the measure of fluorescence activity associated with calcium signaling, or techniques such as fluorescence resonance energy transfer (FRET). Functional assays are preferred since they are less prone to false positive hits. High throughput assays refer to assays that allow the screening of between 10,000 and 100,000 compounds per day. Ultra-high throughput assays refer to assays that allow the screening of over 100,000 compounds per day.

High throughput screening through these libraries is well known in the art as a method to rapidly scan and analyze these libraries. A key factor for success of high throughput searching is the design of the library itself and whether the design increases a probability of retrieving promising lead compounds. The chemical libraries used in the art could basically be categorized into two types: experimental chemical libraries and virtual chemical libraries. Experimental chemical libraries comprise of real chemical compounds that are screened in vitro. Virtual chemical libraries comprise 3-dimensional representations of chemical compounds that are screened computationally (in silico). These two kinds of libraries often complement each other.

In one embodiment of the present invention the candidate compounds can be designed de novo based on identification of certain compounds that have the ability to bind to and/or fit in the model of PERK or its fragments. Earlier in the art, virtual libraries consisted of large set of compounds, often chosen randomly, without giving consideration to rational design directed specifically to the target molecule. The libraries were more-or-less a random collection of compounds. Essentially, the basic approach was to screen as many compounds, in a given period of time, as possible against the target molecule. These libraries typically could include up to one million small-molecule compounds, which were screened relatively quickly in perhaps a few days to a week of run time. The general belief was that drug leads could be derived from the sheer number of compounds screened. Although these efforts led to some notable successes in finding drug leads, it is believed that the screening results are not as fruitful as expected.

In order to improve the capability of finding drug leads against the target, the present invention is directed towards specific design of virtual libraries, where compounds, their parts, or fragments are selectively identified based upon interaction criteria, such as hydrogen bonding, van der waals interactions, electrostatic interactions, and used to generate target libraries. The compound memberships are based on design strategies such as diversity-oriented design and/or target-oriented design.

The goal of diversity-oriented design is to generate libraries with a highly diverse set of chemical compounds. By using a diverse set of compounds, there should be a greater likelihood that query molecules will "hit" one or several novel target compounds. Numerous methods are available for creating such diversity. Skeletal diversity, for example, is a strategy where the core, backbone, or scaffold elements of chemical compounds are chosen to maximize their variation in 3D shape, electrostatics, or molecular properties. Stereochemical diversity involves the 3D spatial arrangements of atoms and functional groups in molecules, and is maximized such that a range of molecular conformations is sampled during screening runs. Molecular property diversity is another method for generating compound diversity. Here, molecular properties available for modification include hydrogen bond donor groups, hydrogen bond acceptor groups, polarizable groups, charge distributions, hydrophobic and lipophobic groups, and numerous other chemical or physical properties. The diversity of the libraries resulting from these methods is often measured using statistical techniques, such as cluster analysis and principal components analysis.

Target-oriented design seeks to create libraries that are focused around specific chemotypes, molecular species, or classes of compounds. Target-oriented design results in focused libraries with a limited number of well-defined compounds. For example, scaffold compounds can be used as "seed" elements with various functional groups systemically added to the seed scaffolds to create sets of analogue compounds. Target-oriented design methods use 3D shape, 3D electrostatics, pharmacophore models, molecular descriptors, and other methods to generate focused libraries. And if compounds of known 3D structure bind to active sites, they can also be used as seeds for libraries. When building targeted libraries, a common design method is to take existing drug leads and generate neighbors (analogues) of the leads in chemistry space using combinatorial methods and conformational expansions of the lead compounds. The resulting compound libraries thus include many analogues of the lead compounds, which can be used in additional screens for novel leads.

Whether virtual high throughput screening (vHTS) libraries are designed for diversity or focused around specific chemotypes, they often use molecular property profiles in the design process. Generally, chemical compounds need to satisfy a variety of constraints before they become marketable drugs, for example, solubility, oral bioavailability, cell membrane permeability, liver enzyme activity (i.e. the cytochrome series), plasma protein binding, penetration of the blood-brain barrier, toxicity (mutagenicity, carcinogenicity, LD50), and many others. For example, a common design approach is focusing molecular properties around Lipinski's rules. This is a set of rules that describes common molecular properties of many currently marketed drugs. Lipinski's rules place limits on molecular weight, the number of hydrogen bond donors and acceptors, the number of rotatable bonds, and solubility. Applying Lipinski's rules in library design acts as a molecular property filter, you can effectively restrict the set of compounds to those with drug-like characteristics.

Compounds in these in silico libraries can also be screened for their ability to interact with the target by using their respective atomic co-ordinates in automated docking algorithms. An automated docking algorithm is one which permits the prediction of interactions of a number of compounds with a molecule having a given atomic structure.

Suitable docking algorithms include: DOCK (Kuntz et al., "A Geometric Approach to Macromolecule-ligand Interactions," *J Mol Biol.* 161(2):269-88 (1982), which is hereby incorporated by reference in its entirety), AUTODOCK (Goodsell et al. *Proteins: Structure, Function and Genetics* 8:195-202 (1990), which is hereby incorporated by reference in its entirety), MOE-DOCK (Chemical Computing Group, Montreal Canada) or FLEXX (BioSolveIT GmbH, Sankt Augustine, Germany). Docking algorithms can also be used to verify interactions with ligands designed de novo.

De novo compound design can also involve a process whereby binding surfaces or sequences within a target macromolecule (e.g., a nucleic acid or polypeptide) are determined, and those surfaces are used as a platform or basis for the rational design of compounds such that the compounds will interact with those surfaces. The molecular modeling steps used in the methods of the invention may use the atomic co-ordinates of PERK or its fragments, and models derived there from, to determine binding surfaces. This preferably reveals essential molecular interactions, for example, van der Waals contacts, electrostatic interactions, and/or hydrogen bonding.

These binding surfaces will typically be used by grid-based techniques (e.g. GRID (Goodford, P. J., "A Computational Procedure for Determining Energetically Favourable Binding Sites on Biologically Important Macromolecules," *J. Med.*

*Chem*, 28: 849-857 (1985), which is hereby incorporated by reference in its entirety), CERIUS² (Accelrys, San Diego, Calif.) and/or multiple copy simultaneous search (MCSS) techniques (Miranker et al., "Functionality Maps of Binding Sites: A Multiple Copy Simultaneous Search Method," *Proteins, Structure, Function and Genetics* 11: 29-34 (1991); Caflish et al., "Multiple Copy Simultaneous Search and Construction of Ligands in Binding Sites: Application to Inhibitors of HIV-1 Aspartic Proteinase," *J. Med. Chem.* 36: 2142-2167 (1993); Eisen et al., "HOOK: A Program for Finding Novel Molecular Architectures that Satisfy the Chemical and Steric Requirements of a Macromolecule Binding Site," *Proteins Structure, Function and Genetics* 19: 199-221 (1994), which are hereby incorporated by reference in their entirety) to map favorable interaction positions for functional groups. This preferably reveals positions in PERK for interactions such as, but not limited to, those with protons, hydroxyl groups, amine groups, hydrophobic groups (e.g. methyl, ethyl, benzyl) and/or divalent cations. The term "functional group" refers to chemical groups that interact with one or more sites on an interaction surface of a macromolecule. A "small molecule" is a compound having molecular mass of less than 3000 Daltons, preferably less than 2000 or 1500, still more preferably less than 1000, and most preferably less than 600 Daltons. A "small molecule fragment" is a portion of a small molecule that has at least one functional group. A "small organic molecule" is a small molecule that comprises carbon.

In one embodiment of the present invention, the designing comprises linking functional groups or small molecule fragments of the identified compounds to form de novo compounds. Once functional groups or small molecule fragments which can interact with specific sites in the binding surface of the target have been identified, they can be linked in a single compound using either bridging fragments with the correct size and geometry or frameworks which can support the functional groups at favorable orientations, thereby providing a compound according to the present invention. Whilst linking of functional groups in this way can be done manually, perhaps with the help of software such as QUANTA (Accelrys, San Diego, Calif.) or SYBYL (Tripos Inc., St. Louis, Mo.), the following software may be used for assistance: HOOK (Eisen, et al., "HOOK: A program for finding novel molecular architectures that satisfy the chemical and steric requirements of a macromolecule binding site," *Proteins Structure, Function and Genetics* 19: 199-221 (1994), which is hereby incorporated by reference in its entirety), which links multiple functional groups with molecular templates taken from a database, and/or CAVEAT (Lauri, G. et al., "CAVEAT: A Program to Facilitate the Design of Organic Molecules," *J. Comp. Aided Mol. Design* 8: 51-66 (1994), which is hereby incorporated by reference in its entirety), which designs linking units to constrain acyclic molecules.

Other computer-based approaches to de novo compound design that can be used with the 3-dimensional atomic coordinates include LUDI (Bohm, H. J., "The Computer Program LUDI: A New Method for the de novo Design of Enzyme Inhibitors," *J. Comp. Aided Molec. Design*, 6: 61-78 (1992), which is hereby incorporated by reference in its entirety), SPROUT (Valerie et al., "Sprout: Recent Developments in the de novo Design of Molecules," *J. Chem. Inf. Comput. Sci.* 34:207-217 (1994); Valerie et al., "Sprout: A Program for Structure Generation," *J. Comput.-Aided Mol. Design* 7:127-153 (1993), which are hereby incorporated by reference in their entirety) and LEAPFROG™ (Tripos Inc., St. Louis, Mo.).

As well as using de novo design, a pharmacophore of the target molecule, for example PERK and its fragments, can be defined i.e. a collection of chemical features and 3D constraints that expresses specific characteristics responsible for biological activity. The pharmacophore preferably includes surface-accessible features, more preferably including hydrogen bond donors and acceptors, charged/ionizable groups, and/or hydrophobic patches. These may be weighted depending on their relative importance in conferring activity (Han Van de Waterbeemd, *Computer Assisted Lead Finding and Optimization* Wiley-VCH (1997), which is hereby incorporated by reference in its entirety).

Pharmacophores can be determined using software such as CATALYST (including HypoGen or HipHop) (Accelrys, San Diego, Calif.), CERIUS² (Accelrys, San Diego, Calif.), or constructed by hand from a known conformation of a lead compound. The pharmacophore can be used to screen in silico compound libraries, using a program such as CATALYST (Accelrys, San Diego, Calif.). Langer et al. provides a discussion on the generation and use of virtual compound libraries, and on studies in which chemical feature-based pharmacophore models are used in combination with in silico screening (Langer et al., "Chemical Feature-based Pharmacophores and Virtual Library Screening for Discovery of New Leads," *Curr Opin Drug Discov Devel.* 6: 370-6 (2003), which is hereby incorporated by reference in its entirety). These procedures are generally used to obtain hits (or leads) that are more likely to give successful clinical candidates against a target molecule(s) of the present invention.

Suitable in silico libraries include commercially or publicly available chemical libraries, for example, the Available Chemical Directory (MDL Inc), the Derwent World Drug Index (WDI), BioByteMasterFile, the National Cancer Institute database (NCI), and the Maybridge catalog can also be used for the purposes of the present invention.

Evaluation of Candidate Compounds

The methods according to the present invention involve evaluating contact between the candidate compounds and the model to determine which of the one or more candidate compounds have an ability to bind to and/or fit in the model of PERK or its fragments. The evaluation of the candidate compounds, which may be a part of a library of compounds, is a central task in the drug-design process. The evaluation of candidate compounds is a means to assess the binding properties of the candidate compounds and ascertain the most promising candidates. There are many ways known in the art which can be used to evaluate the candidate compounds and are described (Kitchen et al., "Docking and Scoring in Virtual Screening for Drug Discovery: Methods and Applications," *Nature Reviews. Drug Discovery* 3: 935-49 (2004); Lengauer et al., "Computational Methods for Biomolecular Docking," *Curr. Opin. Struct. Biol.* 6: 402-6 (1996); Wei et al., "Testing a Flexible-receptor Docking Algorithm in a Model Binding Site," *J. Mol. Biol.* 337: 1161-82 (2004); Meng et al., "Automated Docking with Grid-based Energy Evaluation," *Journal of Computational Chemistry* 13: 505-524 (2004); Morris et al., "Automated Docking Using a Lamarckian Genetic Algorithm and an Empirical Binding Free Energy Function," *Journal of Computational Chemistry* 19: 1639-1662 (1998); Schneider et al., "Computer based de novo Design of Drug-like Molecules," *Nature Reviews* 4:649-663, which are hereby incorporated by reference in their entirety). Scoring functions can rank the candidate compounds based on their binding to the target and also provide a guide during the design process through the search space.

In one embodiment of the present invention, the binding and/or interactions between the candidate drug and a model of PERK or its relevant parts are evaluated using automated docking algorithms.

Without any intentions of limiting the methods that can be used for the purposes of evaluating the candidate compounds and their interactions with PERK or its fragments, the evaluation methods can be broadly categorized into: steric scoring, receptor based scoring, and ligand based scoring.

In the steric scoring, for example, the evaluation of the candidate compounds can be done based on a simple steric constraints to guide the selection process (Lewis et al., "Automated Site-directed Drug Design Using Molecular Lattices," *J. Mol. Graphics* 10:66-78 (1992); Roe et al., "BUILDER v.2: Improving the Chemistry of a de novo Design Strategy," *J. Comput. Aided Mol. Des.* 9:269-282 (1995); Tschinke, et al., "The NEWLEAD Program: A New Method for the Design of Candidate Structures from Pharmacophoric Hypothesis," *J. Med. Chem.* 36:3863-3870 (1993); Lewis et al., Automated Site-directed Drug Design: The Formation of Molecular Templates in Primary Structure Generation," *Proc. R. Soc. Lond. B* 236:141-162 (1989); Gillett, et al., "Automated Structure Design in 3D," *Tetrahedron Comput. Method.* 3:681-696 (1990); Lewis, R. A. Automated Site-directed Drug Design: Approaches to the Formation of 3D Molecular Graphs," *J. Comput. Aided Mol. Des.* 4:205-210 (1990); Rotstein, et al., "GenStar: A Method for de novo Drug Design," *J. Comput. Aided. Mol. Des.* 7:23-43 (1993), which are hereby incorporated by reference in their entirety).

Receptor based scoring can be sub-divided into explicit force field methods, empirical scoring functions, and knowledge based scoring functions. These methods attempt to approximate the binding free energy (Schneider et al., "Computer based de novo Design of Drug-like Molecules," *Nature Reviews* 4:649-663, which is hereby incorporated by reference in its entirety). Force fields are computationally more costly than the other two types of scoring functions. LEGEND (Nishibata et al., "Automatic Creation of Drug Candidate Structures Based on Receptor Structure. Starting Point for Artificial Lead Generation," *Tetrahedron* 47:8985-8990 (1991), which is hereby incorporated by reference in its entirety) was the first program that used a force field to evaluate candidate compounds. Many others now use this to evaluate candidate compounds (Rotstein et al., "GroupBuild: A Fragment Based Method for de novo Drug Design," *J. Med. Chem.* 36: 1700-1710 (1993); Luo et al., "RASSE: A New Method for Structure-based Drug Design," *J. Chem. Inf. Comput. Sci.* 36: 1187-1194 (1996); Pearlman et al., "CONCERTS: Dynamic Connection of Fragments as an Approach to de novo Ligand Design," *J. Med. Chem.* 39: 1651-1663 (1996); Liu et al., "Structure-based Ligand Design by Dynamically Assembling Molecular Building Blocks at Binding Site," *Proteins* 36: 462-470 (1999); Zhu, et al., Design of Selective Inhibitors of Cyclooxygenase-2 Dynamic Assembly of Molecular Building Blocks," *J. Comput. Aided Mol. Des.* 15: 447-463 (2001); Zhu et al., "Structure-based Ligand Design for Flexible Proteins: Application of New F-Dyco Block," *J. Comput. Aided Mol. Des.* 15: 979-996 (2001), which are hereby incorporated by reference in their entirety). Empirical scoring functions are a weighted sum of individual ligand-receptor interaction types, usually supplemented by penalty terms, for example, the number of rotatable bonds. These methods are fast and have proven suitability for de novo design methods and programs (Clark et al., "PRO_LIGAND: An Approach to de novo Molecular Design. 1. Application to the Design of Organic Molecules," *J. Comput. Aided Mol. Des.* 9: 13-32 (1995); Murray et al., "PRO_SELECT: Combining Structure Based Drug Design and Combinatorial Chemistry for Rapid Lead Discovery. 1. Technology," *J. Comp. Aided Mol. Des.* 11: 193-207 (1997); Bohacek et al., "Multiple Highly Diverse Structures Complementary to Enzyme Binding Sites: Results of Extensive Application of a de novo Design Method Incorporating Combinatorial Growth," *J. Am. Chem. Soc.* 116: 5560-5571 (1994); Wang et al., "LigBuilder: A Multi-purpose Program for Structure-based Drug Design," *J. Mol. Model.* 6: 498-516 (2000); Pearlman et al., "CONCEPTS: New Dynamic Algorithm for de novo Design Suggestion," *J. Comput. Chem.* 14: 1184-1193 (1993); Eldridge et al., "Empirical Scoring Functions: I. The Development of a Fast Empirical Scoring Function to Estimate the Binding Affinity of Ligands in Receptor Complexes," *J. Comput. Aided Mol. Des.* 11: 425-445 (1997), which are hereby incorporated by reference in their entirety). Knowledge-based scoring is grounded on a statistical analysis of ligand-receptor complex structures. The frequencies of each possible pair of atoms in contact to each other are determined. Interactions found to occur more frequently than would be randomly expected are considered attractive; interactions that occur less frequently are considered repulsive. A de novo design program, SmoG, uses implementation of this type of scoring function (DeWitte et al., "SMoG de novo Design Method Based on Simple, Fast, and Accurate Free Energy Estimates. 1. Methodology and Supporting Evidence," *J. Am. Chem. Soc.* 118: 11733-11744 (1996); Ishchenko et al., "Small Molecule Growth 2001 (SMoG2001): An Improved Knowledge Based Scoring Function for Protein-ligand Interactions," *J. Med. Chem.* 45: 2770-2780 (2002), which are hereby incorporated by reference in their entirety).

If a three-dimensional structure of a particular biological target is unavailable but one or more binding molecules are known, ligand-based scoring provides an alternative strategy. Receptor-based structure generation has a huge conformational complexity. A ligand-based strategy, in contrast, can either consider the three-dimensional or the topological structure of one or more known ligands. One way to use the information inherent to the known actives is the derivation of a three-dimensional ligand pharmacophore model. Once established, it can be used to obtain a pseudo-receptor model (Waszkowycz et al., "PRO_LIGAND: An Approach to de novo Molecular Design. 2. Design of Novel Molecules from Molecular Field Analysis (MFA) Models and Pharmacophores," *J. Med. Chem.* 37: 3994-4002 (1994), which is hereby incorporated by reference in its entirety). This facilitates the application of de novo design programs that were originally developed with a receptor-based strategy in mind to ligand-based design.

Alternatively, the three-dimensional ligand pharmacophore model can be used directly in a similarity design method (Waszkowycz et al., "PRO_LIGAND: An Approach to de novo Molecular Design. 2. Design of Novel Molecules from Molecular Field Analysis (MFA) Models and Pharmacophores," *J. Med. Chem.* 37: 3994-4002 (1994), which is hereby incorporated by reference in its entirety). Whereas a (pseudo) receptor guides the design of structures that are complementary to the primary target constraints, a ligand pharmacophore model can be applied to designing structures that are similar to these constraints. A set of known ligands can also be taken as an input for the development of a target-specific quantitative structure-activity relationship (QSAR) model. The established model then serves as a scoring function (Nachbar et al., "Molecular Evolution: Automated Manipulation of Hierarchical Chemical Topology and its Application to Average Molecular Structures," *Genet. Programming Evolvable*

*Machines* 1: 57-94 (2000); Pellegrini et al., "Development and Testing of a de novo Drug-design Algorithm," *J. Comp. Aided Mol. Des.* 17: 621-641 (2003); Douguet et al., "A Genetic Algorithm for the Automated Generation of Small Organic Molecules: Drug Design Using an Evolutionary Algorithm," *J. Comput. Aided Mol. Des.* 14: 449-466 (2000), which are hereby incorporated by reference in their entirety). Identification of Compounds The methods of the present invention also comprise identifying the compounds which, based on evaluation, have the ability to bind to and/or fit in the model as compounds potentially useful for inhibiting PERK. Candidate compounds can be identified using any of the techniques mentioned supra such as screening, de novo design, molecular modeling, and contacting the compound with PERK and/or its fragments and assaying the interaction between them. Scoring functions described above may be used to provide a cut off limit and used to assist in identification of compounds with increased potential to inhibit PERK. Various other criteria such as contact area, binding energy calculations, free energy calculations, visual inspection, evaluation of steric hindrances and hydrogen bonding potential can be used to identify compounds with potential to inhibit PERK.

Various methods which use in vitro or in vivo assaying the activity of an PERK or other similar kinases in the presence of a compound are well known in the art and can be used to indentify the compounds and/or to rank compounds according to their inhibition potential. The most widely used technique for measuring protein kinase activity is based on radioactive detection. In this method, a sample containing the kinase is incubated with activators and a substrate in the presence of gamma $^{32}$P-ATP. After a suitable incubation period, the reaction is stopped and an aliquot of the reaction mixture is placed directly onto a filter which binds the substrate. The filter is then washed multiple times to remove excess radioactivity, and the amount of radiolabelled phosphate incorporated into the substrate is measured by scintillation counting. Similarly, the detection can also be done after running the substrate on a electrophoretic gel and scanning the gel for radioactivity due to gamma $^{32}$P-ATP. This method is widely used and provides an accurate method for determining protein kinase activity in both crude and purified samples.

Other methods for detecting kinase activity in the presence of compounds are based on separations due to the charge differences between phosphorylated and non-phosphorylated proteins and peptides. In these respects, techniques based on gel electrophoresis and HPLC have, among others, been used. In combination with these techniques, spectrophotometric and fluorometric detection have been used. Descriptions of many methods used for detecting protein kinase activity can be found in WO 93/10461 and U.S. Pat. No. 5,120,644, U.S. Pat. No. 5,763,198, and U.S. Pat. No. 5,141,852, which are hereby incorporated by reference in their entirety. Detection of the phosphorylation of eIF2α can also be carried out using an antibody or antigen-binding fragment. Any of the alternative methods of detecting phosphorylation in proteins that are known in the art are also suitable.

In addition, phosphorylation can also be detected indirectly by measuring the depletion of ATP from the reaction as described by Munagala et al., Identification of Small Molecule Ceramide Kinase Inhibitors Using a Homogeneous Chemiluminescence High Throughput Assay," *Assay Drug Dev Tech* 5:65-73 (2007), which is hereby incorporated by reference in its entirety. Alternatively, the incorporation of labeled ATP (i.e. $^{32}$P-ATP) into the protein substrate, as described herein, can also be measured.

The above method of identifying compounds useful for inhibiting PERK activity can be carried out using a whole cell sample. Any eukaryotic or prokaryotic cell sample expressing a substrate protein is suitable for use, including mammalian, insect (e.g., *D. melangaster*), amphibian (e.g., *X. laevis*), fungi (e.g., yeast), or bacteria cells.

In another aspect, the present relates to a pharmaceutical composition comprising a compound selected from the group consisting of:

(1) a compound of formula (I):

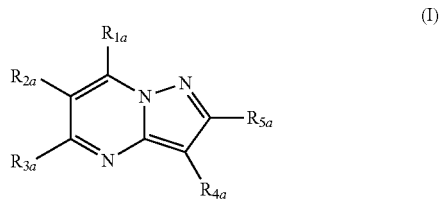

wherein:

$R_{1a}$ is independently H, halogen, $CF_3$, $CHF_2$, $CH_2F$, $OR_{6a}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen;

$R_{2a}$ and $R_{4a}$ are independently H, halogen, $C_1$-$C_6$ alkyl, $C_2$-$C_6$ alkenyl, or $C_2$-$C_6$ alkynyl;

$R_{3a}$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of $R_{3a}$ optionally substituted from 1 to 4 times for each cyclic ring with substituents selected from the group consisting of H, $OR_{6a}$, —C(O)$R_{6a}$, —C(O)O$R_{6a}$, —C(O)N$R_{6a}R_{7a}$, —NH$R_{6a}$, —N$R_{6a}R_{7a}$, —S$R_{6a}$, —S(O)$R_{6a}$, —S(O)$_2R_{6a}$, $NH_2$, CN, $NO_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl;

$R_{5a}$ is independently H, —C(O)$R_{6a}$, —C(O)O$R_{6a}$, —C(O)N$R_{6a}R_{7a}$, —S(O)$R_{6a}$, or —S(O)$_2R_{7a}$;

$R_{6a}$ is independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen; and $R_{7a}$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of $R_{7a}$ optionally substituted from 1 to 4 times for each cyclic ring with substituents selected from the group consisting of H, OH, $OR_{6a}$, —C(O)$R_{6a}$, —C(O)O$R_{6a}$, —C(O)N$R_{6a}R_{7a}$, —NH$R_{6a}$, —N$R_{6a}R_{7a}$, —S$R_{6a}$, —S(O)$R_{6a}$, —$NO_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl;

(2) a compound of formula (II):

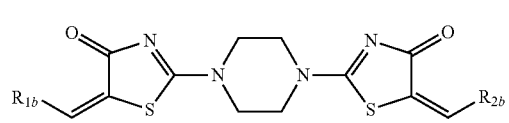

(II)

wherein:

- $R_{1b}$ and $R_{2b}$ are independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of $R_{1b}$ or $R_{2b}$ optionally substituted from 1 to 4 times for each cyclic ring with substituents selected from the group consisting of H, OH, $OR_{3b}$, —$C(O)R_{3b}$, —$C(O)OR_{3b}$, —$C(O)NR_{3b}R_{4b}$, —$NHR_{3b}$, —$NR_{3b}R_{4b}$, —$SR_{3b}$, —$S(O)R_{3b}$, $NO_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl; and

- $R_{1b}$ and $R_{2b}$ are independently $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen;

(3) a compound of formula (III):

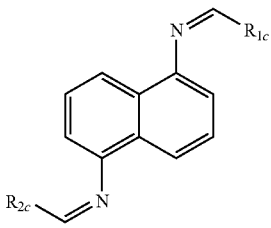

(III)

wherein:

- $R_{1c}$ and $R_{2c}$ are independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of $R_{1c}$ and $R_{2c}$ optionally substituted from 1 to 4 times for each cyclic ring with substituents selected from the group consisting of H, OH, $OR_{3c}$, —$C(O)R_{3c}$, $R_{3c}C(O)O$—, —$C(O)NR_{3c}R_{4c}$, —$NHR_{3c}$, —$NR_{3c}R_{4c}$, —$SR_{3c}$, —$S(O)R_{3c}$, —$S(O)_2R_{3c}$, $NH_2$, CN $NO_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl; and

- $R_{3c}$ and $R_{4c}$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen;

(4) a compound of formula (IV):

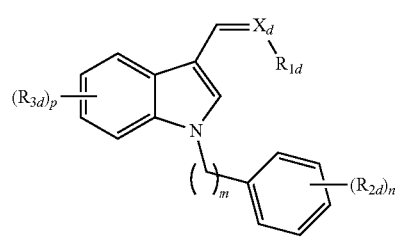

(IV)

wherein:

- $X_d$ is N or $CR_{4d}R_{5d}$;
- m, n, or p are integers from 0 to 5;
- $R_{1d}$ is independently H or $R_{6d}C(O)N(R_{7d})$—;
- $R_{2d}$ and $R_{3d}$ are independently H, halogen, $OR_{4d}$, $C_1$-$C_6$ alkyl, $C_2$-$C_6$ alkenyl, or $C_2$-$C_6$ alkynyl;
- $R_{4d}$ and $R_{5d}$ are combined to form a substituted or unsubstituted mono or polycyclic heteroaryl containing from 1 to 5 heteroatoms selected from the group consisting of oxygen, nitrogen, and sulfur, each mono or polycyclic heteroaryl optionally substituted from 1 to 4 times for each cyclic ring with substituents selected from the group consisting of H, OH, $NH_2$, CN, $NO_2$, halogen, oxo, thio, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl; and
- $R_{6d}$ and $R_{7d}$ are independently H, $C_1$-$C_6$ alkyl, $C_2$-$C_6$ alkenyl, $C_2$-$C_6$ alkynyl, a substituted or unsubstituted mono or polycyclic heteroaryl containing from 1 to 5 heteroatoms selected from the group consisting of oxygen, nitrogen, and sulfur, each one of $R_{6d}$ and $R_{7d}$ optionally substituted from 1 to 3 times with substituents selected from the group consisting of OH, $NH_2$, CN, $NO_2$, halogen, oxo, thio, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl;

(5) a compound of formula (V):

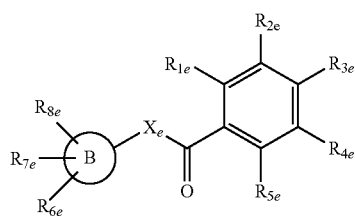

(V)

wherein:

- B represents a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of B optionally substituted from 1 to 4 times for each cyclic ring with substituents selected from the group consisting of OH, $NH_2$, CN, $NO_2$, halogen, oxo, thio, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and mono or polycyclic aryl;
- $X_e$ represents O or $NR_{9e}$;
- $R_{1e}$, $R_{2e}$, $R_{3e}$, $R_{4e}$, and $R_{5e}$ are independently H, halogen, $OR_{9e}$, $R_{9e}C(O)NH$—, $C_1$-$C_6$ alkyl, $C_2$-$C_6$ alkenyl, or $C_2$-$C_6$ alkynyl;

$R_{6e}$, $R_{7e}$, and $R_{8e}$ are independently H, halogen, OH, NH$_2$, —CR$_{9e}$=NR$_{10e}$, arylalkyl, C$_1$-C$_6$ alkyl, C$_2$-C$_6$ alkenyl, C$_2$-C$_6$ alkynyl, a substituted or unsubstituted mono or polycyclic heteroaryl containing from 1 to 5 heteroatoms selected from the group consisting of oxygen, nitrogen, and sulfur, each one of $R_{6e}$, $R_{7e}$, or $R_{8e}$ optionally substituted from 1 to 3 times with substituents selected from the group consisting of OH, NH$_2$, CN, NO$_2$, halogen, C$_1$-C$_6$ alkyl, C$_1$-C$_6$ alkoxy, C$_2$-C$_6$ alkenyl, C$_2$-C$_6$ alkynyl, C$_3$-C$_6$ cycloalkyl, C$_4$-C$_7$ cycloalkylalkyl, and mono or polycyclic aryl;

$R_{9e}$ is independently H, C$_1$-C$_6$ alkyl, C$_2$-C$_6$ alkenyl, C$_2$-C$_6$ alkynyl, a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each one of $R_{9e}$ optionally substituted from 1 to 3 times with substituents selected from the group consisting of OH, NH$_2$, CN, NO$_2$, halogen, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, and mono or polycyclic aryl;

$R_{10e}$ is independently H or $R_{12e}$C(O)NR$_{13e}$—; and $R_{12e}$ and $R_{13e}$ are independently H, C$_1$-C$_6$ alkyl, C$_2$-C$_6$ alkenyl, or C$_2$-C$_6$ alkynyl, each one of $R_{12e}$ and $R_{13e}$ optionally substituted from 1 to 4 times with substituents selected from the group consisting of OH, OR$_{9e}$, NH$_2$, CN, NO$_2$, halogen, oxo, thio, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, and mono or polycyclic aryl; and (6) a compound of formula (VI):

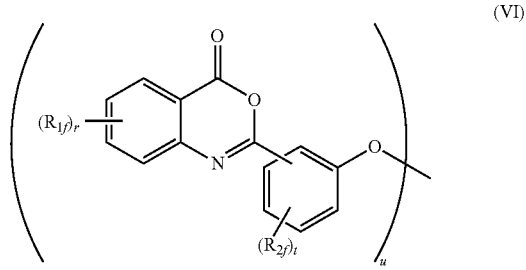

(VI)

wherein:
u is an integer 2 or 4;
r and t are integers from 1 to 4; and
$R_{1f}$ and $R_{2f}$ are independently H, halogen, NO$_2$, CN, C$_1$-C$_6$ alkoxy, C$_1$-C$_6$ alkyl, C$_2$-C$_6$ alkenyl, or C$_2$-C$_6$ alkynyl.

As used above, and throughout the description of the present invention, the following terms, unless otherwise indicated, shall be understood to have the following meanings. If not defined otherwise herein, all technical and scientific terms used herein have the same meaning as is commonly understood by one of ordinary skill in the art to which this invention belongs. In the event that there is a plurality of definitions for a term herein, those in this section prevail unless stated otherwise.

The term "halo" or "halogen" means fluoro, chloro, bromo, or iodo.

The term "optionally substituted" indicates that a group may have a substituent at each substitutable atom of the group (including more than one substituent on a single atom), and the identity of each substituent is independent of the others.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is oxo (i.e., =O), then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent. Exemplary substitutents include, without limitation, oxo, thio (i.e. =S), nitro, cyano, halo, OH, NH$_2$, C$_1$-C$_6$ alkyl, C$_1$-C$_6$ alkoxy, C$_2$-C$_6$ alkenyl, C$_2$-C$_6$ alkynyl, C$_3$-C$_6$ cycloalkyl, C$_4$-C$_7$ cycloalkylalkyl, monocyclic aryl, monocyclic hetereoaryl, polycyclic aryl, and polycyclic heteroaryl.

The term "monocyclic" indicates a molecular structure having one ring.

The term "polycyclic" indicates a molecular structure having two or more rings, including, but not limited to, fused, bridged, or spiro rings.

The term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl.

The term "alkoxy" means an alkyl-O—, alkenyl-O—, or alkynyl-O-group wherein the alkyl, alkenyl, or alkynyl group is described above. Exemplary alkoxy groups include methoxy, ethoxy, n-propoxy, i-propoxy, n-butoxy, pentoxy, and hexoxy.

The term "cycloalkyl" refers to a non-aromatic saturated or unsaturated mono- or polycyclic ring system which may contain 3 to 6 carbon atoms; and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane.

The term "cycloalkylalkyl" refers to a radical of the formula —R$^a$R$^b$ where R$^a$ is an alkyl radical as defined above and R$^b$ is a cycloalkyl radical as defined above. The alkyl radical and the cycloalkyl radical may be optionally substituted as defined above.

The term "aryl" refers to aromatic monocyclic or polycyclic ring system containing from 6 to 19 carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "arylalkyl" refers to a radical of the formula —R$^a$R$^b$ where R$^a$ is an alkyl radical as defined above and R$^b$ is an aryl radical as defined above. The alkyl radical and the cycloalkyl radical may be optionally substituted as defined above.

The term "aryarylalkyl" refers to a radical of the formula —R$^a$R$^b$R$^c$ where R$^a$ is an alkyl as defined above, R$^b$ is an aryl radical as defined above, and R$^c$ is an aryl radical as defined above. The alkyl radical and both aryl radicals may be optionally substituted as defined above.

The term "heterocyclyl" refers to a stable 3- to 18-membered ring radical which consists of carbon atoms and from one to five heteroatoms selected from the group consisting of nitrogen, oxygen and sulfur. For purposes of this invention, the heterocyclyl radical may be a monocyclic, or a polycyclic ring system, which may include fused, bridged, or spiro ring systems; and the nitrogen, carbon, or sulfur atoms in the heterocyclyl radical may be optionally oxidized; the nitrogen atom may be optionally quaternized; and the ring radical may be partially or fully saturated. Examples of such heterocyclyl radicals include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone.

The term "heteroaryl" refers to an aromatic ring radical which consists of carbon atoms and from one to five heteroatoms selected from the group consisting of nitrogen, oxygen, and sulfur. For purposes of this invention the heteroarayl may be a monocyclic or polycyclic ring system; and the nitrogen, carbon, and sulfur atoms in the heteroaryl ring may be optionally oxidized; the nitrogen may optionally be quaternized. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl.

Further heterocycles and heteraryls are described in Katritzky et al., eds., "Comprehensive Heterocyclic Chemistry: The Structure, Reactions, Synthesis and Use of Heterocyclic Compounds," Vol. 1-8, Pergamon Press, N.Y. (1984), which is hereby incorporated by reference in its entirety.

The term "compounds of the invention", and equivalent expressions are meant to embrace compounds of formula (I) to (VI) as herein before described, which expression includes the prodrugs, the pharmaceutically acceptable salts, and the solvates, e.g., hydrates, where the context so permits. Similarly, reference to intermediates, whether or not they themselves are claimed, is meant to embrace their salts and solvates, where the context so permits. For the sake of clarity, particular instances, when the context so permits, are sometimes indicated in the text, but these instances are purely illustrative and it is not intended to exclude other instances when the context so permits.

This invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

In another embodiment of the present invention, the pharmaceutical composition comprises a compound is selected from the group consisting of:

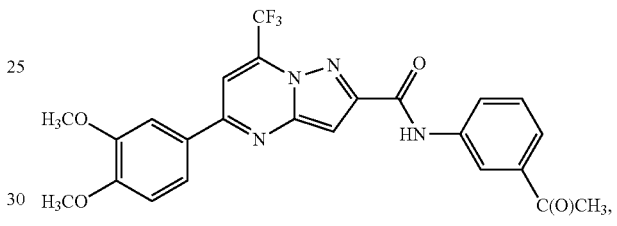
(within formula I)

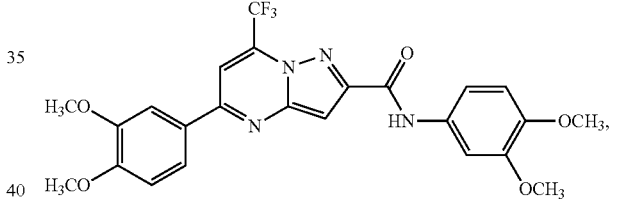
(within formula I)

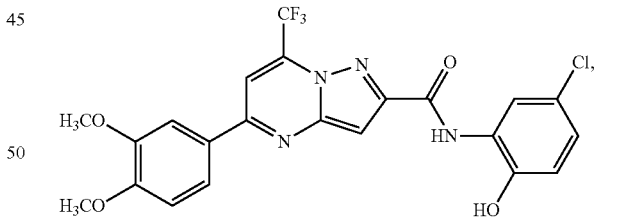
(within formula I)

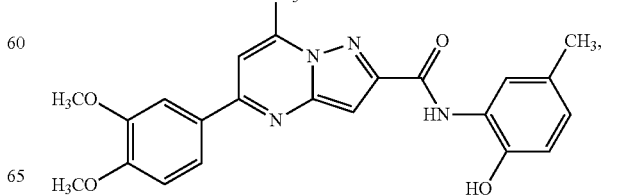
(within formula I)

-continued
(within formula II)
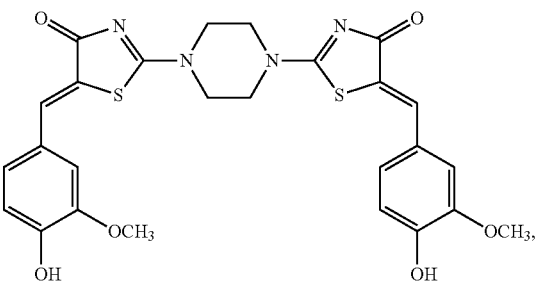
(within formula II)
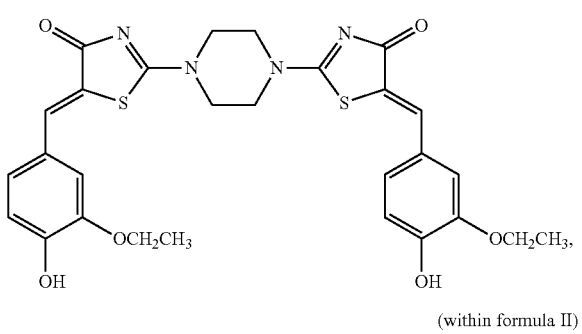
(within formula II)
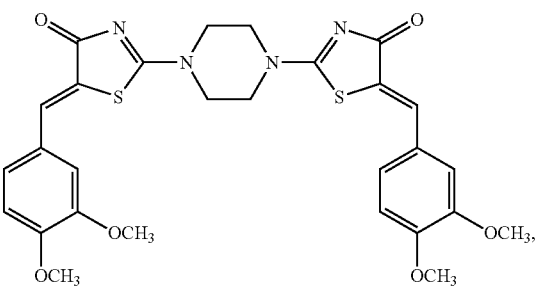
(within formula IV)
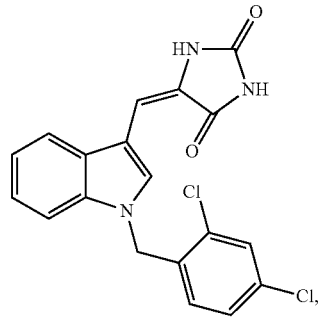
(within formula IV)
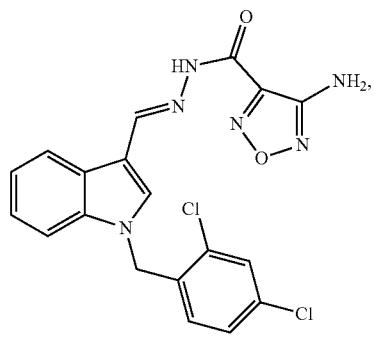
(within formula V)
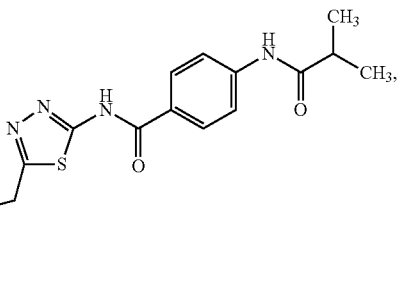
(within formula V)
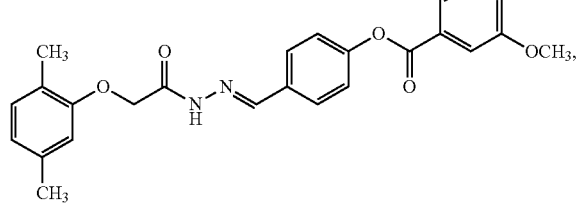
(within formula V)
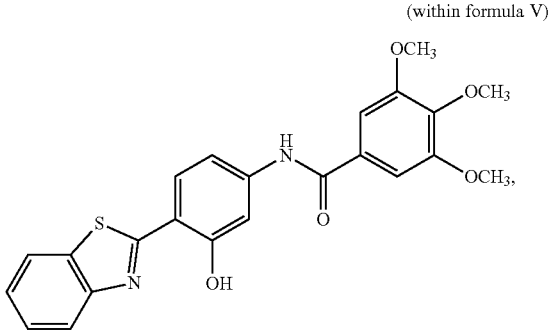
(within formula III)
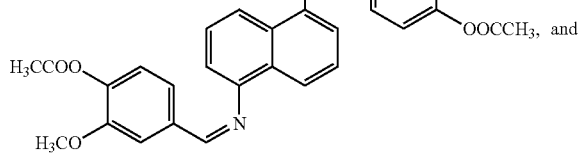
and
(within formula VI)
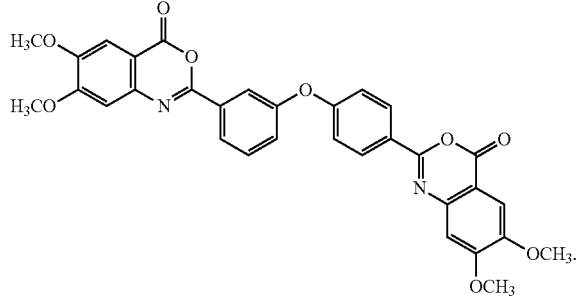
In another embodiment of the present invention, the pharmaceutical composition comprises the selected compound:

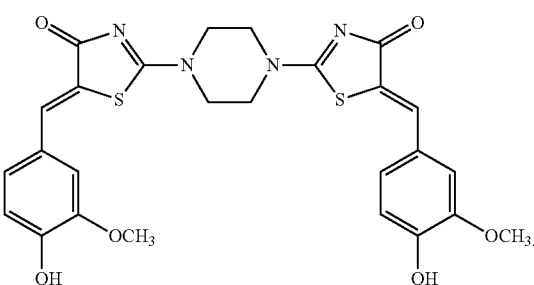 [SMILES: COc1cc(/C=C2\SC(N3CCN(C4=NC(=O)/C(=C/c5ccc(O)c(OC)c5)S4)CC3)=NC2=O)ccc1O]

In another embodiment of the present invention, the pharmaceutical composition comprises the selected compound:

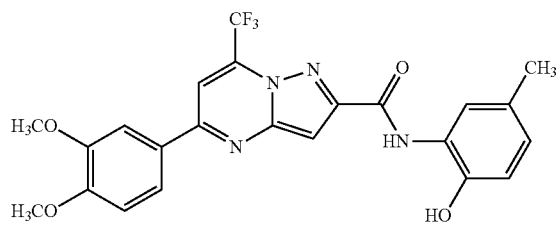 [SMILES: COc1ccc(-c2cc(C(F)(F)F)n3nc(C(=O)Nc4cc(C)ccc4O)cc3n2)cc1OC]

In one embodiment of the present invention, the method comprises screening the identified compounds in vitro for their ability to kill and/or inhibit growth of cancer cells and designating the identified compounds which kill and/or inhibit growth of cancer cells as being cancer therapeutics.

The PERK-mediated condition could be a cancer and can be selected from the group consisting of prostate cancer, cervical cancer, hematological-associated cancer, colon cancer, pancreatic cancer, stomach cancer, myeloma, breast cancer, melanoma, and cancers caused due to defects in the tumor suppressor pathway. The pharmaceutical compounds or the compositions of the present invention can be used for producing oncolytic activity or tumor suppression, including but not limited to chemotherapeutic agents known in the art, radiation and/or antibodies or in conjunction with other agents that are known anticancer agents.

In one embodiment of the present invention, the method comprises screening the identified compounds in vitro for their ability to block the AD pathogenesis inducer BACE1 and designating the identified compounds which block the AD pathogenesis inducer BACE1 as being AD therapeutics. The pharmaceutical compounds or the compositions of the present invention can be used for inhibition of amyloidogenesis. After identifying compounds useful in inhibiting protein kinase-like endoplasmic reticulum protein kinase (PERK) with the above-described models a BACE1 model comprising BACE1 or portions thereof is provided. With this BACE1 model, contact between the identified compounds and the model is analyzed to determine which of the one or more identified compounds have an ability to bind to and/or fit in the BACE1 model. It is then designated, based on said analyzing, which of the identified compounds have the ability to bind to and/or fit in the BACE1 model as compounds potentially useful for treating Alzheimer's disease.

In one embodiment of the present invention, the method comprises screening the identified compounds in vitro for their ability to block the AD pathogenesis inducer BACE1 and designating the identified compounds which block the AD pathogenesis inducer BACE1 as being AD therapeutics. The pharmaceutical compounds or the compositions of the present invention can be used for inhibition of amyloidogenesis. After designating the identified compounds with enhanced potential to inhibit PERK, with the above-identified first and second models, a BACE1 model comprising BACE1 or portions thereof is provided. With this BACE1 model, contact between the designated compounds and the model is analyzed to determine which of the one or more designated compounds have an ability to bind to and/or fit in the BACE1 model. It is then assigned, based on said analyzing, which of the identified compounds have the ability to bind to and/or fit in the BACE1 model as compounds potentially useful for treating Alzheimer's disease.

With this BACE1 model, analyzing contact between the compounds and the model comprising BACE1 or portions thereof to determine which of the one or more identified compounds have an ability to bind to and/or fit in the model comprising BACE1 or portions thereof, and determining the compounds which, based on said analyzing, have the ability to bind to and/or fit in the model comprising BACE1 or portions thereof as compounds potentially useful for treating Alzheimer's disease.

Beta-secretase 1 (BACE1) also known as beta-site APP cleaving enzyme 1 (beta-site amyloid precursor protein cleaving enzyme 1), memapsin-2 (membrane-associated aspartic protease 2), and aspartyl protease 2 (ASP2) is an enzyme that in humans is encoded by the BACE1 gene (Vassar R et al. "Beta-secretase Cleavage of Alzheimer's Amyloid Precursor Protein by the Transmembrane Aspartic Protease BACE," Science 286 (5440): 735-41 (1999); Willem M et al., "Control of Peripheral Nerve Myelination by the Beta-secretase BACE1," Science 314 (5799): 664-6 (2006); Walker L C et al. "Alzheimer Therapeutics-what After the Cholinesterase Inhibitors?" Age Ageing 35 (4): 332-5 (2006); Baxter E W et al. "2-Amino-3,4-dihydroquinazolines as Inhibitors of BACE-1 (beta-site APP cleaving enzyme): Use of Structure Based Design to Convert a Micromolar Hit into a Nanomolar Lead," J. Med. Chem. 50 (18): 4261-4 (2007), which are hereby incorporated by reference in their entirety).

Generation of the 40 or 42 amino acid-long amyloid-β peptides that aggregate in the brain of Alzheimer's patients requires two sequential cleavages of the amyloid precursor protein (APP). Extracellular cleavage of APP by BACE creates a soluble extracellular fragment and a cell membrane-bound fragment referred to as C99. Cleavage of C99 within its transmembrane domain by β-secretase releases the intracellular domain of APP and produces amyloid-β. Since alpha-secretase cleaves APP closer to the cell membrane than BACE does, it removes a fragment of the amyloid-β peptide. Initial cleavage of APP by alpha-secretase rather than BACE prevents eventual generation of amyloid-β (Hong L. et al. "Structural Features of Human Memapsin 2 and Their Biological and Pathological Implications," Acta Biochim. Biophys. Sin. (Shanghai) 36 (12): 787-92 (2005); Johnston J A. et al. "Expression and Activity of Beta-site Amyloid Precursor Protein Cleaving Enzyme in Alzheimer's Disease," Biochem. Soc. Trans. 33 (Pt 5): 1096-100 (2006); Dominguez D. I. et al. "BACE1 and Presenilin: Two Unusual Aspartyl Proteases Involved in Alzheimer's Disease," Neuro-degenerative diseases 1 (4-5): 168-74 (2006); Zacchetti D et al. "BACE1 Expression and Activity: Relevance in Alzheimer's Disease," Neuro-degenerative diseases 4 (2-3): 117-26 (2007), which are hereby incorporated by reference in their entirety).

In another aspect the present invention relates to a method of treating a PERK-mediated condition in a subject. This method comprises selecting a subject with the PERK-mediated condition, providing a compound which binds to/fits in a first model comprising the PERK active domain, where the active domain is selected from the group consisting of the peptide spanning from amino acid residue Asp144 to amino acid residue Ser191 of SEQ ID NO: 1 and peptides comprising the amino acid residue at position 7 of SEQ ID NO: 1 and administering the compound to the selected subject under conditions effective to treat the PERK-mediated condition in the subject.

In one embodiment the method also involves selecting a candidate compound that additionally binds to and/or fits in a second model comprising a peptide comprising amino acid residue Aspartate-144 (SEQ ID NO: 1).

There are multiple disturbances that can cause accumulation of unfolded proteins in the endoplasmic reticulum (ER), triggering a unfolded protein reponse (UPR) (Ron et al., "Signal Integration in the Endoplasmic Reticulum Unfolded Protein Response," *Nature Reviews Mol Cell Biol* 8:519-529 (2007); Malhotra et al., "The Endoplasmic Reticulum and the Unfolded Protein Response," *Semin Cell Dev Biol* 18:716-731 (2007), which are hereby incorporated by reference in their entirety). The PERK-mediated condition could be, for example, cancer, neurodegenerative disease due to inclusion body formation or protein aggregation, stroke, ischemia reperfusion injury, bipolar disorder, heart disease, types-1 and 2 diabetes, and immune disorders.

In another aspect the present invention relates to a method of treating a PERK-mediated condition in a subject which comprises selecting a subject with the PERK-mediated condition, providing a pharmaceutical composition as described supra, and administering the composition to the selected subject under conditions effective to treat the PERK-mediated condition in the subject.

The PERK-mediated condition could be a neurodegenerative disease due to inclusion body formation or protein aggregation for example Alzheimer's disease, juvenile onset Parkinson's disease, amyotrophic lateral sclerosis, Huntington's disease, and prion related diseases. In a preferred embodiment the PERK-mediated condition is Alzheimer's disease. The PERK-mediated condition could be a heart disease for example myocardial ischemia, cardiac hypertrophy, heart failure, and atherosclerosis.

The PERK-mediated condition could be an antibody based autoimmune disorders and dendritic cell dysfunction. The immune disorder could be, for example, rheumatoid arthritis, myositis, multiple sclerosis, ankylosing spondalitis, and inflammatory bowel disease.

As will be apparent to one of ordinary skill in the art, administering any of the pharmaceutical compound or composition of the present invention may be carried out using generally known methods. Typically, the agents of the present invention can be administered orally, parenterally, for example, subcutaneously, intravenously, intramuscularly, intraperitoneally, by intranasal instillation, by application to mucous membranes, such as, that of the nose, throat, and bronchial tubes or by direct contact to the cells of a subject, by direct injection into the subjects cells or by intratumoral injection. They may be administered alone or with suitable pharmaceutical carriers, and can be in solid or liquid form such as, tablets, capsules, powders, solutions, suspensions, or emulsions. The amount of vector(s) to be administered will depend on several factors, such as route of administration, the condition of the individual, stage of the disease, and the degree of aggressiveness of the malignancy, if the disease is cancer. Effective doses of the pharmaceutical compound or composition of the present invention may also be extrapolated from dose-response curves derived from animal model test systems. Also, the pharmaceutical compound or composition may be used in conjunction with other treatment modalities. Formulations also include lyophilized and/or reconstituted forms of the vectors (including those packaged as a virus) of the present invention.

The pharmaceutical compounds or compositions of the present invention may include a pharmaceutically acceptable carrier or excipient. Pharmaceutically acceptable carriers are well known in the art and include but are not limited to saline, buffered saline, dextrose, water, glycerol, sterile isotonic aqueous buffer, and combinations thereof. One example of such an acceptable carrier is a physiologically balanced culture medium containing one or more stabilizing agents such as stabilized, hydrolyzed proteins, lactose, etc. The carrier is preferably sterile. The formulation should suit the mode of administration.

The pharmaceutical compounds or compositions of the present invention may be orally administered, for example, with an inert diluent, with an assimilable edible carrier, enclosed in hard or soft shell capsules, compressed into tablets, or incorporated directly with the food of the diet. Such compositions and preparations should contain at least 0.1% of active compound. The percentage of the active agent or compound in these compositions may, of course, be varied and may conveniently be between about 2% to about 60% of the weight of the unit. The amount of active agent in such therapeutically useful compositions is such that a suitable dosage will be obtained. Preferred compositions according to the present invention are prepared so that an oral dosage unit contains between about 1 and 250 mg of active compound.

Pharmaceutically acceptable carriers for oral administration are well known in the art and include but are not limited to saline, buffered saline, dextrose, water, glycerol, sterile isotonic aqueous buffer, and combinations thereof. One example of such an acceptable carrier is a physiologically balanced culture medium containing one or more stabilizing agents such as stabilized, hydrolyzed proteins, lactose, etc. The carrier is preferably sterile. The formulation should suit the mode of administration. The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as fatty oil.

Various other materials may be present as coatings or to modify the physical form of the dosage unit. For instance, tablets may be coated with shellac, sugar, or both.

These pharmaceutical compounds or compositions may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms. Formulations for parenteral and non-parenteral drug delivery are known in the art and are set forth in *Remington's Pharmaceutical Sciences,* 19th Edition, Mack Publishing (1995), which is hereby incorporated by reference in its entirety.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The agents of the present invention may also be administered directly to the airways in the form of an aerosol. For use as aerosols, the agents of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Suitable subjects to be treated in accordance with the present invention include human and non-human animals, preferably mammals or avian species. Exemplary mammalian subjects include, without limitation, humans, non-human primates, dogs, cats, rodents, cattle, horses, sheep, and pigs. Exemplary avian subjects include, without limitation chicken, quail, turkey, duck or goose. In a preferred embodiment the subject is human.

The present invention is illustrated, but not limited, by the following examples.

EXAMPLES

Example 1

Methods Used for Homology Modeling

In the present invention, the computational work on homology modeling, virtual library screening (VLS) and chemoinformatics was done using ICM software produced by Molsoft, LLC (La Jolla, Calif.) (Abagyan et al., "ICM—A New Method for Protein Modeling and Design: Applications to Docking and Structure Prediction from the Distorted Native Conformation," *J Comp Chem* 15:488-506 (1994), which is hereby incorporated by reference in its entirety). Two crystal structures of eIF2α kinase GCN2 (PDB code: 1zy4 & 1zy5) were chosen as the templates for modeling the PERK catalytic domain. The two homology models were initially built using the ICM method (Cardozo et al., "Homology Modeling by the ICM Method," *Proteins* 23:403-14 (1995), which is hereby incorporated by reference in its entirety), followed by sampling of the activation loop. This ensemble of multiple receptor conformations was used for subsequent docking experiments. The residues were numbered starting from the N-terminus of the catalytic domain of PERK as residue number 1 of SEQ ID NO: 1, which is equivalent to residue 589 of SEQ ID NO: 3.

The quality of the global structure of the models was validated in terms of Z-scores by the WHAT-IF program (Vriend G., "WHAT IF: A Molecular Modeling and Drug Design Program," *J Mol Graph* 8:52-6 (1990), which is hereby incorporated by reference in its entirety). The local structural reliability of the models was assessed by calculation of the energy strain in ICM, which is represented by normalized residue energy (NRE) (Maiorov et al., "Energy Strain in Three-Dimensional Protein Structures," *Fold Des* 3:259-69 (1998), which is hereby incorporated by reference in its entirety). Energy strain can detect steric clashes, exposed hydrophobic areas and other physicochemical anomalies that are invisible in graphical views of the structure (Cardozo et al., "Druggability of SCF Ubiquitin Ligase-Protein Interfaces," *Methods Enzymol* 399:634-53 (2005), which is hereby incorporated by reference in its entirety). In addition to the energy strain calculation, the ATP analogue AMPPNP was docked to the PERK model and compared to its template (PDB code: 1zy5), followed by the calculation of the root mean square deviation (RMSD) value for heavy atoms between the docked AMPPNP in PERK and the co-crystallized AMPPNP in eIF2α kinase GCN2. The contacts between the docked AMPPNP and PERK were further analyzed to assess the local structural quality.

Example 2

Structure-Based Database Search

ICM-based virtual library screening is based on fast docking of a flexible ligand to a grid representation of the receptor followed by an evaluation of the docked conformation with a scoring function. The ICM scoring function takes into account conformational entropy loss and solvation electrostatic energy change (Cavasotto et al., "Protein Flexibility in Ligand Docking and Virtual Screening to Protein Kinases," *J Mol Biol* 337:209-25 (2004), which is hereby incorporated by reference in its entirety), which are critical for accuracy of the scoring function. The ATP binding site in PERK homology models was initially screened against a collection of 315,102 compounds of the ChemBridge Express Library (San Diego, Calif.). Compounds with a docking score less than or equal to −32 were filtered by hydrogen bonds and van der Waals contacts, followed by hierarchical clustering according to chemical similarity. After visual inspection, the selected compounds were subsequently evaluated for their ability to inhibit PERK-mediated eIF2α phosphorylation in vitro using the assay described in Example 5.

Example 3

Identification of Structural Determinants of PERK Inhibition from Compounds Tested In Vitro Residues making contact with the ligand were analyzed for each of the active and inactive compounds. The Wilcoxon rank sum test (Wilcoxon, F. "Individual Comparisons by Ranking Methods," *Biometrics Bulletin* 1:80-83 (1945), which is hereby incorporated by reference in its entirety) was performed to identify the difference on van der Waals contact area with certain residues between the two groups.

Example 4

Confirmation of Structural Determinants of PERK Inhibition from Compounds Tested In Vitro Compounds with similar chemical groups but little or no Met-7 residue contact were subsequently generated by substructure search through the ChemBridge library using part of the compound as a scaffold. The scaffolds included the chemical architecture not making Met-7 contact in the corresponding active compound. The compounds retrieved from the substructure search were then screened against the PERK homology models, followed by the calculation of Met-7 contact area. All the small molecules with a Met-7 contact area lower than 10 Å² were identified as the chemically similar, Met-7-mismatched compounds. Each active PERK inhibitor was paired with a single most chemically similar, Met-7-contact-negative compound. A similar procedure was performed to identify a chemically similar, contact-negative comparison group for the activation loop contact and Asp-144.

Example 5

In Vitro Kinase Inhibition Assay

Mouse PERK proteins comprising the cytoplasmic portion of the molecule with the delta loop deleted were pre-incubated with varying concentrations of compound at room temperature for 10 minutes. This construct thus contains close to a minimal catalytic domain of PERK, closely similar but not identical to SEQ ID NO: 1. The kinase reaction was initiated by the addition of 2 µM ATP, 0.2 µM γ-[$^{32}$P]ATP, 10 µM eIF2α and allowed to proceed at room temperature for 15 minutes (Marciniak et al., "Activation-Dependent Substrate Recruitment by the Eukaryotic Translation Initiation Factor 2 Kinase PERK," *J Cell Biol* 172: 201-9 (2006), which is hereby incorporated by reference in its entirety). The phosphorylated eIF2α was then separated on 14% SDS-PAGE and visualized by autoradiography. To determine the selectivity of the compounds, their ability to inhibit protein kinase PKA was also evaluated. Briefly, PKA was pre-incubated with the compound at 40 µM, the highest concentration used in the PERK assay, for 10 minutes. Then, 10 µM ATP, 0.2 µM γ-[$^{32}$P]ATP and 10 µM GSTag were added, followed by the incubation at room temperature for 15 minutes.

Example 6

Homology Model

Two structures of the catalytic domain of eIF2α kinase GCN2 (PDB code: 1zy4 & 1zy5) were selected as the templates as they have a highly statistically significant structural homology (P=10e-21) (Abagyan et al., "Do Aligned Sequences Share the Same Fold?" *J Mol Biol* 273:355-68 (1997), which is hereby incorporated by reference in its entirety). In addition, these two crystal structures have high resolution and low temperature factors in the ATP binding site, suggesting the good structural quality of these two templates at that location. Given that loop modeling is less accurate and the conformational rearrangement of the activation loop upon ligand binding is crucial for kinase activity, the PERK activation loop was further sampled and an ensemble of multiple loop conformations was subsequently generated and used for docking. The structural quality of the models, analyzed using the WHAT-IF program, energy strain analysis and cross docking with known ligand, indicated that the structural quality in the ATP binding site in the PERK models was reliable for structure-based virtual screening.

Example 7

Initial Virtual Library Screening

The objective was to uncover specific structure-activity relationships in the active site of PERK, including the identification of the structural determinants of ligand activity, selectivity and potency. VLS screening of 315,102 compounds in the ChemBridge library against the two PERK homology models was initially carried out. All compounds with a docking score less than or equal to −32 (Schapira et al., "Rational Discovery of Novel Nuclear Hormone Receptor Antagonists," *Proc Natl Acad Sci USA* 97:1008-13 (2000), which is hereby incorporated by reference in its entirety) were further filtered by hydrogen bonds, van der Waals contacts, followed by hierarchical clustering and visual inspection. The selected compounds were then subjected to the evaluation on their ability to inhibit PERK-mediated eIF2α phosphorylation in vitro using the assay described in Example 5. Six compounds were detected as active by in vitro kinase inhibition, while the other six compounds were found to be inactive (Table 1).

TABLE 1

Met-7 Contact Area in the active and inactive compounds

| Compound | Structure | Activity | Met-7 Contact Area (Å²) |
|---|---|---|---|
| A4 | 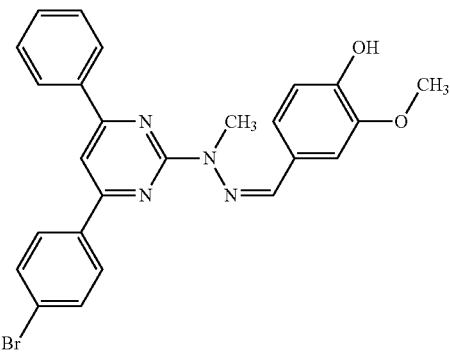 [SMILES: COc1cc(/C=N\N(C)c2nc(-c3ccccc3)cc(-c3ccc(Br)cc3)n2)ccc1O] | active | 21.6 |

TABLE 1-continued

Met-7 Contact Area in the active and inactive compounds

| Compound | Structure | Activity | Met-7 Contact Area (Å$^2$) |
|---|---|---|---|
| B2 | 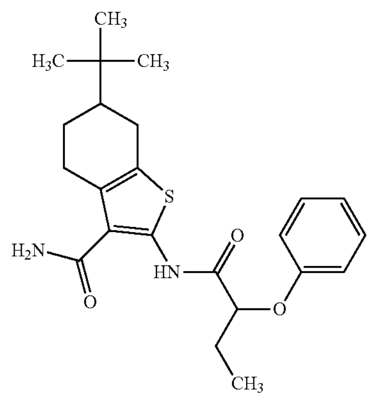 [SMILES: CCC(Oc1ccccc1)C(=O)Nc1sc2c(c1C(N)=O)CCC(C(C)(C)C)C2] | active | 22.9 |
| B6 | 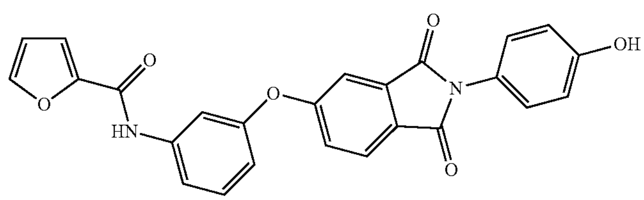 [SMILES: O=C(Nc1cccc(Oc2ccc3c(c2)C(=O)N(c2ccc(O)cc2)C3=O)c1)c1ccco1] | active | 22.1 |
| C1 | 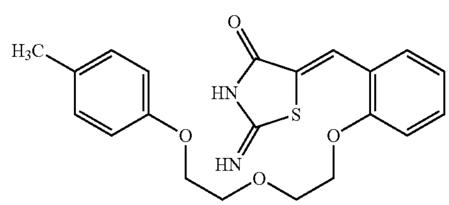 [SMILES: Cc1ccc(OCCOCCOc2ccccc2/C=C2\SC(=N)NC2=O)cc1] | active | 22.8 |
| D1 | 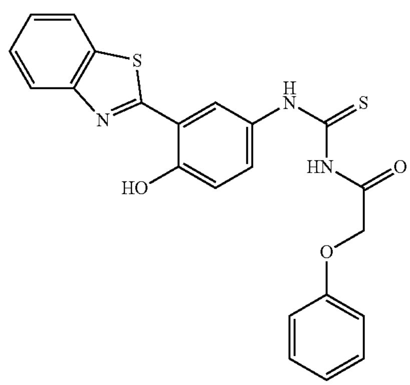 [SMILES: O=C(COc1ccccc1)NC(=S)Nc1ccc(O)c(-c2nc3ccccc3s2)c1] | active | 32.6 |
| E1 | 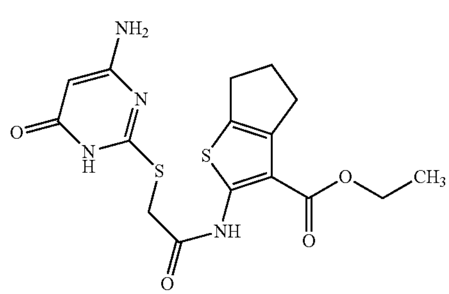 [SMILES: CCOC(=O)c1c(NC(=O)CSc2nc(N)cc(=O)[nH]2)sc2c1CCC2] | active | 29.7 |

TABLE 1-continued

Met-7 Contact Area in the active and inactive compounds

| Compound | Structure | Activity | Met-7 Contact Area (Å$^2$) |
|---|---|---|---|
| A1 | 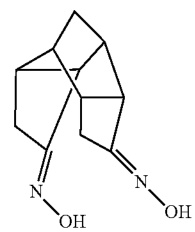 [SMILES: ON=C1CC2C3CC(C12)C1/C(=N\O)CC31] | inactive | 11.1 |
| A2 | 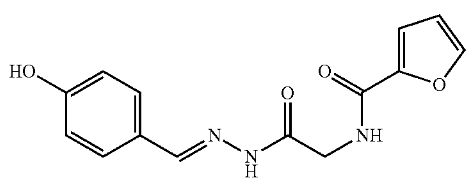 [SMILES: O=C(CNC(=O)c1ccco1)N/N=C/c1ccc(O)cc1] | inactive | 5.3 |
| A3 | 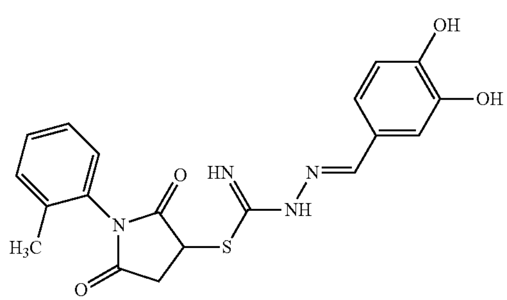 [SMILES: Cc1ccccc1N1C(=O)CC(SC(=N)N/N=C/c2ccc(O)c(O)c2)C1=O] | inactive | 2.2 |
| C3 | 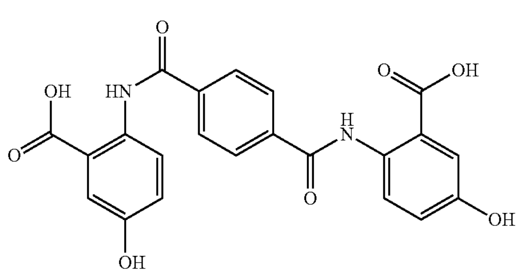 [SMILES: O=C(Nc1ccc(O)cc1C(=O)O)c1ccc(C(=O)Nc2ccc(O)cc2C(=O)O)cc1] | inactive | 11.5 |

TABLE 1-continued

Met-7 Contact Area in the active and inactive compounds

| Compound | Structure | Activity | Met-7 Contact Area (Å$^2$) |
|---|---|---|---|
| C6 | 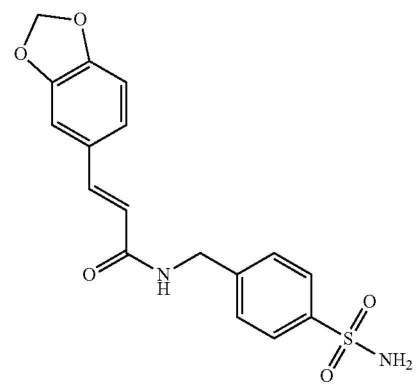 [SMILES: NS(=O)(=O)c1ccc(CNC(=O)/C=C/c2ccc3c(c2)OCO3)cc1] | inactive | 14.7 |
| D4 | 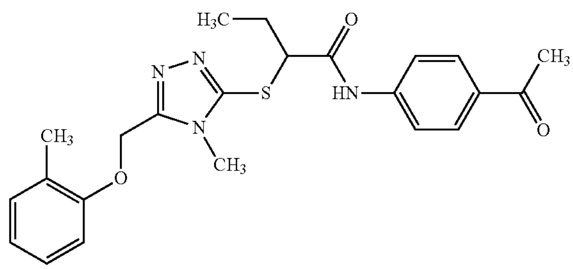 [SMILES: CCC(Sc1nnc(COc2ccccc2C)n1C)C(=O)Nc1ccc(C(C)=O)cc1] | inactive | 0 |

The comparative receptor-ligand atomic interactions between the active and inactive group of compounds were further analyzed. The difference in Met-7 van der Waals contact area between the active and inactive compounds was statistically significant (p value=0.0022) (Table 1, FIGS. 1A & 1C), suggesting that van der Waals contact of the compound with Met-7 in PERK might be critical for the activity.

Example 8

A Met-7 Van Der Waals Contact is a Structural Determinant of PERK Inhibition

To further validate the hypothesis that Met-7 contact is a structural determinant of PERK inhibition in vitro, a set of corresponding compounds with a similar chemical architecture but little or no Met-7 contact upon docking was generated. As expected, these compounds were inactive in vitro (FIGS. 1B and 1D), suggesting the indispensable role of strong van der Waals contact (>20 Å$^2$) with Met-7 in PERK inhibitor design. Notably, none of the six active compounds in the initial VLSI were selective for PERK when compared to PKA (FIG. 1E). Thus, Met-7 is a structural determinant to distinguish between the active and inactive compounds for PERK, but is not itself a determinant of selectivity for PERK. The criteria used to judge selectivity is lack of or severely reduced inhibition by a compound acting directly at the kinase ATP site of at least one other kinase known to be active in cells accompanied by inhibition of PERK by that same compound acting directly at PERK's ATP site.

Example 9

Figure 2:
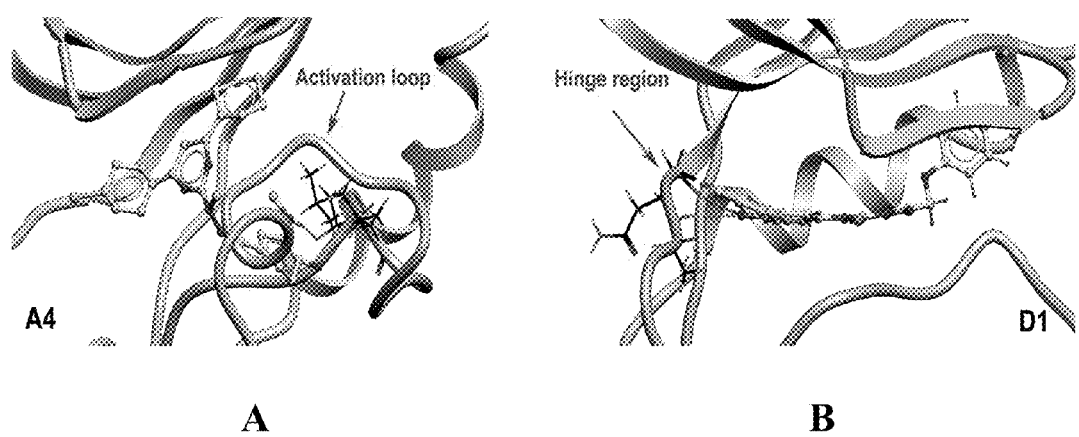
FIGS. 2A-B show the structural interactions of compounds A4 and D1 with PERK.

The N-Terminal Portion of the PERK Activation Loop Area is a Structural Determinant of Selectivity for PERK Inhibitors Among the six active compounds in the initial VLS screening, A4 and D1 showed relatively stronger inhibition of PERK. However, compound A4 displayed the inhibition within a narrow range of concentration, while D1 exhibited an activity varying over a range of 1-25 μM. Interestingly, the analysis of the predicted structural interactions of these two compounds with PERK showed that A4 makes hydrogen bonds with two residues Leu-147 and Val-148 in SEQ ID NO: 1 or SEQ ID NO: 2 (equivalent to Leu-956 and Val-957 in SEQ ID NO: 3) at the origin of the activation loop, while D1 interacts with the hinge region (FIGS. 2A-B). It was hypothesized that A4 exhibits a slight cooperative effect in PERK inhibition due to its interaction with the stem of the activation loop. The activation loop, adjacent to the ATP binding pocket, is critical for the transition between active and inactive conformation of kinases (see the schematic of PERK sequence showing the ATP binding pocket (residues 7, 8, 10, 13, 15, 28 and 30) in italics and the activation loop (residues 144-191) in bold).

```
 1  FEPIQQMGRG GFGVVFEAKN KVDDCNYAIK RIRLPNRELA REKVMREVKA

51  LAKLEHPGIV RYFNAWLETK VYLYIQMQLC RKENLKDWMN RRCSLEDREH
```

```
101 GVCLHIFLQI AEAVEFLHSK GLMHRDLKPS NIFFTMDDVV KVGDFGLVTA

151 MDQDEEEQTV LTPMPAYATH TGQVGTKLYM SPEQIHGNNY SHKVDIFSLG

201 LILFELLYPF STLMERVRIL TDVRNLKFPL LFTQKYPQEH MMVQDMLSPS

251 PTERPEATDI IENAIFENLE FPGKTVLR
```

Moreover, this area contains a PERK-specific amino acid sequence. Activation loops in kinases have been known to influence activity at active sites in dimerized or oligomerized domains nearby by cross-domain contact (Taylor et al., "PKR and eIF2α: Integration of Kinase Dimerization, Activation, and Substrate Docking," *Cell* 122:823-5 (2005), which is hereby incorporated by reference in its entirety), suggesting a structural basis for cooperativity in an inhibition that contacts the activation loop.

Figure 3:
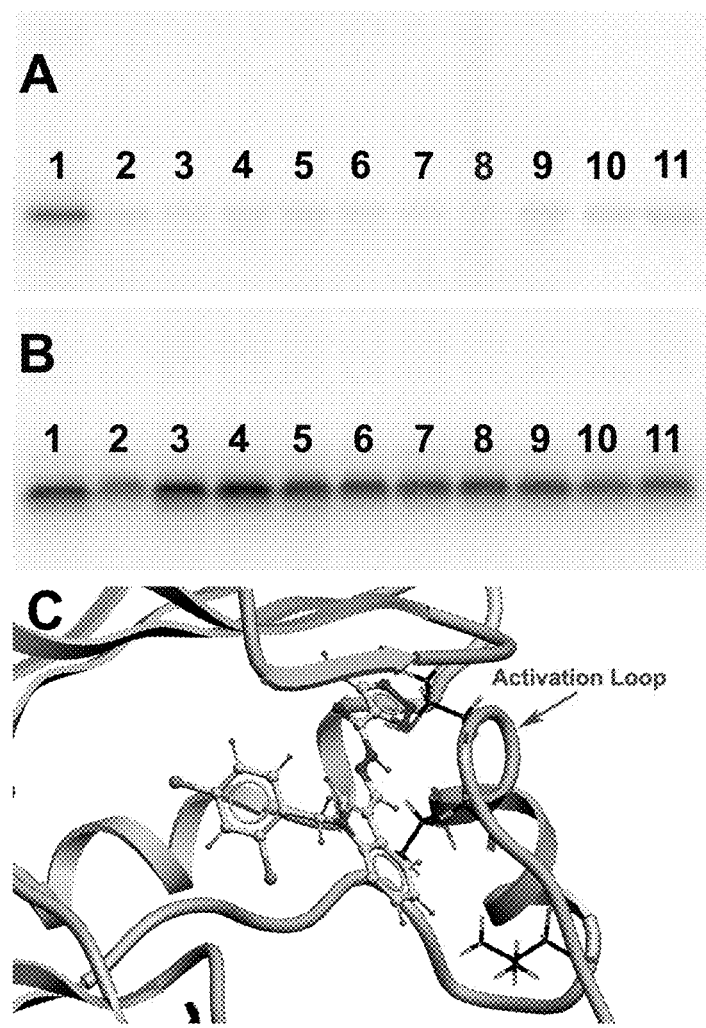
FIGS. 3A-C show improved selectivity by screening the activation loop area. Equivalently, the amino acid present at this structural location in human PERK, regardless of whether they are the same in mouse, may be viewed as a structural determinant to distinguish between active and inactive compounds against human PERK.

VLS sampling of the area in the PERK model near the activation loop was carried out in order to test this hypothesis. Nine compounds making extensive contacts with the N-terminal portion of the activation loop, including hydrogen bonding and van der Waals contacts, were subsequently selected for in vitro assay and were found to be active. Notably, none of these compounds showed significant inhibition of PKA, while the inhibition of PERK was maintained (FIG. 3).

Example 10

Figure 4:
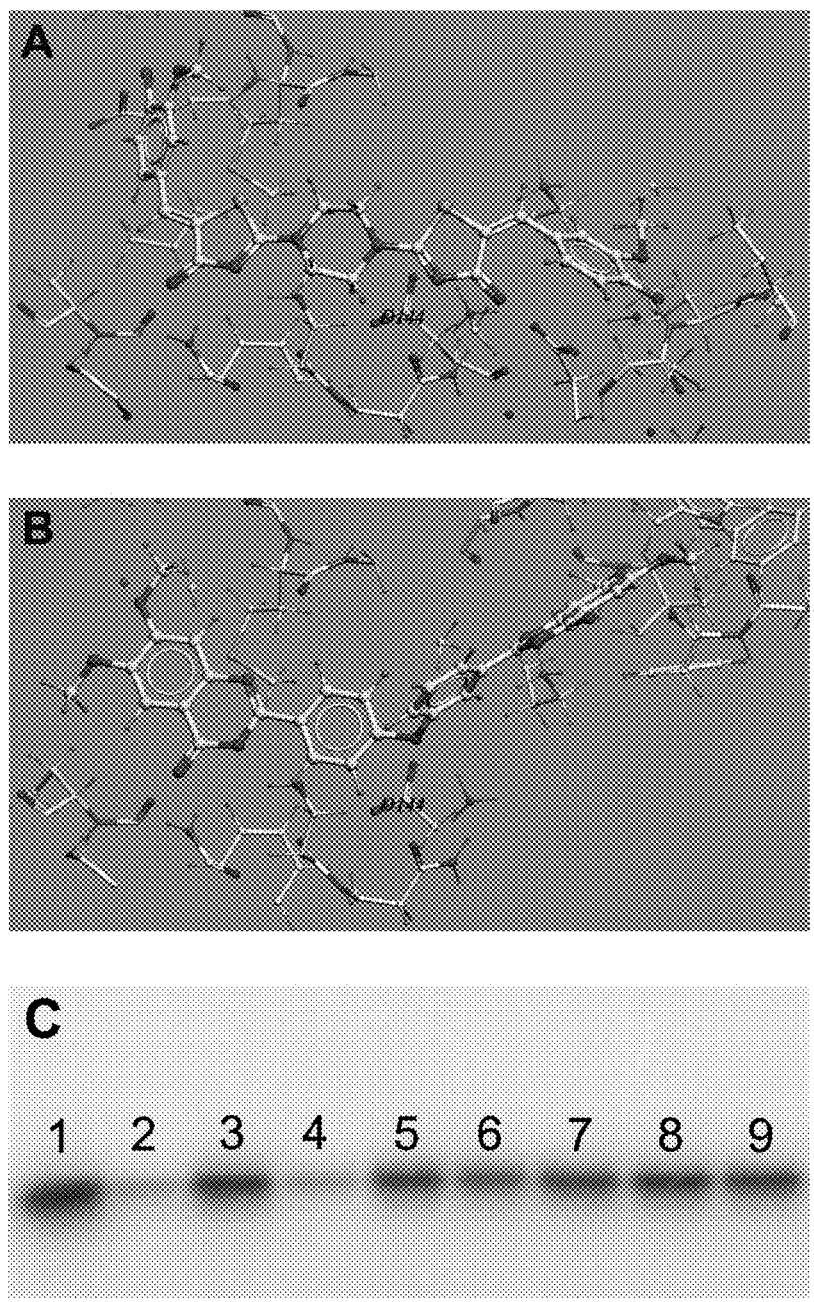
FIGS. 4A-C show that the electrostatic complementarity to aspartic acid 144 (Asp-144) side chain is important for compound potency. Residues surrounding the ligand within a sphere of 6 Å are displayed as stick and balls.

Electrostatic Complementarity to Asp-144 Side Chain is a Structural Determinant of PERK Inhibitor Potency The $IC_{50}$ of all the PERK selective compounds were determined. Interestingly, seven showed an $IC_{50}$ less than 10 µM, while one compound displayed an $IC_{50}$ of 30 µM. To identify the structural determinant accounting for this potency difference, the atomic interactions with their surrounding residues within 6 Å were further analyzed. All the compounds with an $IC_{50}$ less than 10 µM have partial positive charge of nitrogen in the midsection of the compound scaffold, providing electrostatic complementarity to the negative charge of the side-chain carboxyl group displayed in the PERK active site by Asp-144 (FIG. 4A). On the contrary, the one compound with an $IC_{50}$ of 30 µM exhibited a partial negative charge in its scaffold midsection (FIG. 4B). Aspartate-144 is part of the DFG motif—a crucial triad of kinase activation loops. Thus, electrostatic complementarity to Asp-144 side chain might be a structural determinant of PERK inhibitor potency. To validate this hypothesis, seven corresponding compounds with similar chemical groups but partial negative charges in their scaffold midsections were subsequently generated. Five compounds were inactive in vitro (FIG. 4C), while two were weakly active with an $IC_{50}$ more than 25 µM. This finding, therefore, indicates that electrostatic complementarity to Asp-144 side chain is important for PERK inhibitory potency, which is consistent with a recent study on the identification of a novel inhibitor of the JAK2 tyrosine kinase (Kiss et al., "Identification of a Novel Inhibitor of JAK2 Tyrosine Kinase by Structure-Based Virtual Screening," *Bioorg Med Chem Lett* 19:3598-601 (2009), which is hereby incorporated by reference in its entirety).

Example 11

Active Compounds Act as ATP Competitive Inhibitors

Figure 5:
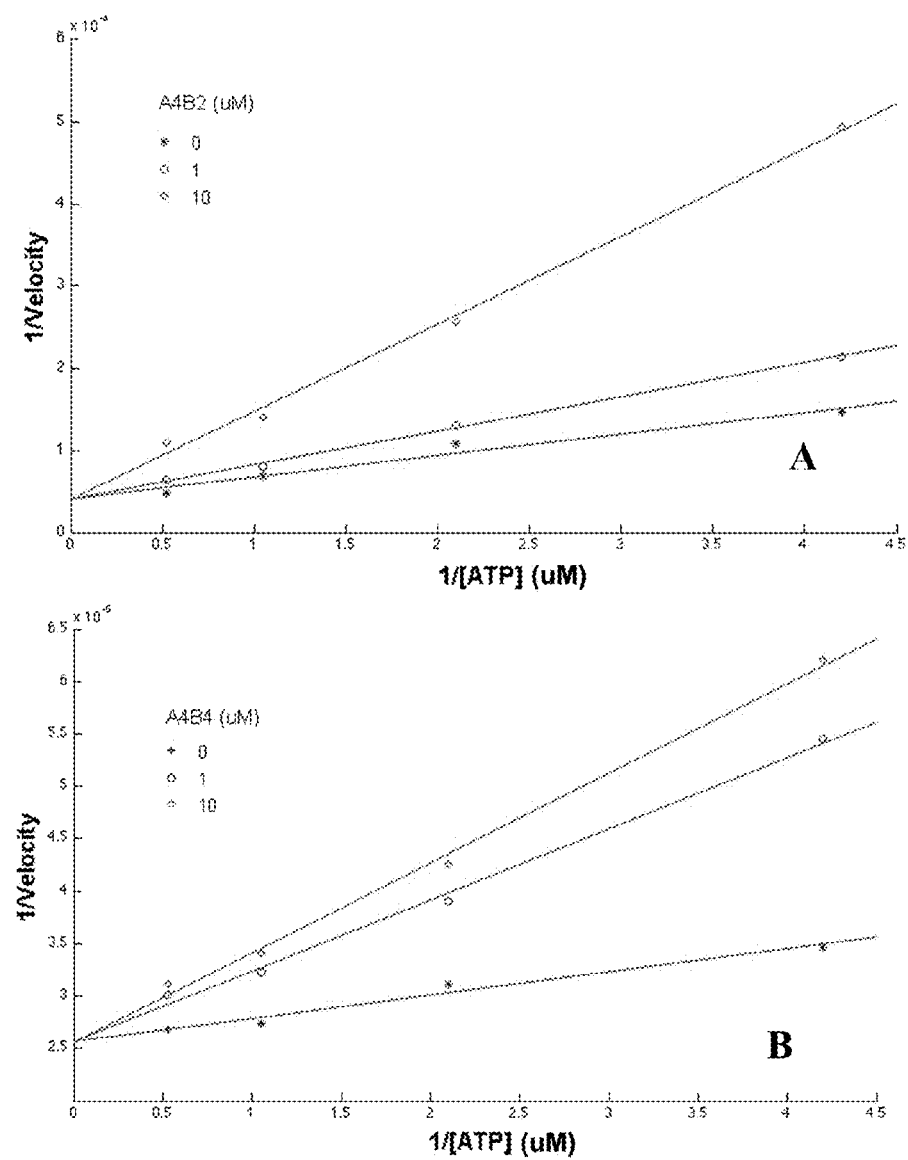
FIGS. 5A-B show the Lineweaver Burke plot of ATP competition for compounds A4B2 and A4B4, respectively. Initial reaction velocity was expressed as the phosphorylation of the substrate eIF2α. The curves were generated using linear least squares fitting model in MatLab. All concentrations are expressed as µM.

The small molecular inhibitors of the present invention were designed to block PERK activity via binding to the ATP binding site, which includes Met-7 and Asp-144 among the amino acid side chains lining the ATP binding pocket. To examine whether they act as ATP competitive inhibitors, the inhibitory potency of A4B2 and A4B4, two compounds with an $IC_{50}$ of 1 µM in vitro, was evaluated for PERK activity by introduction of different concentrations of ATP. Lineweaver Burke plots for PERK inhibition by A4B2 and A4B4 with respect to different ATP concentrations showed that increasing the concentration of inhibitors results in a family of lines with a common y-intercept but with different slopes, which is indicative of competitive inhibition (FIG. 5).

Figure 6:
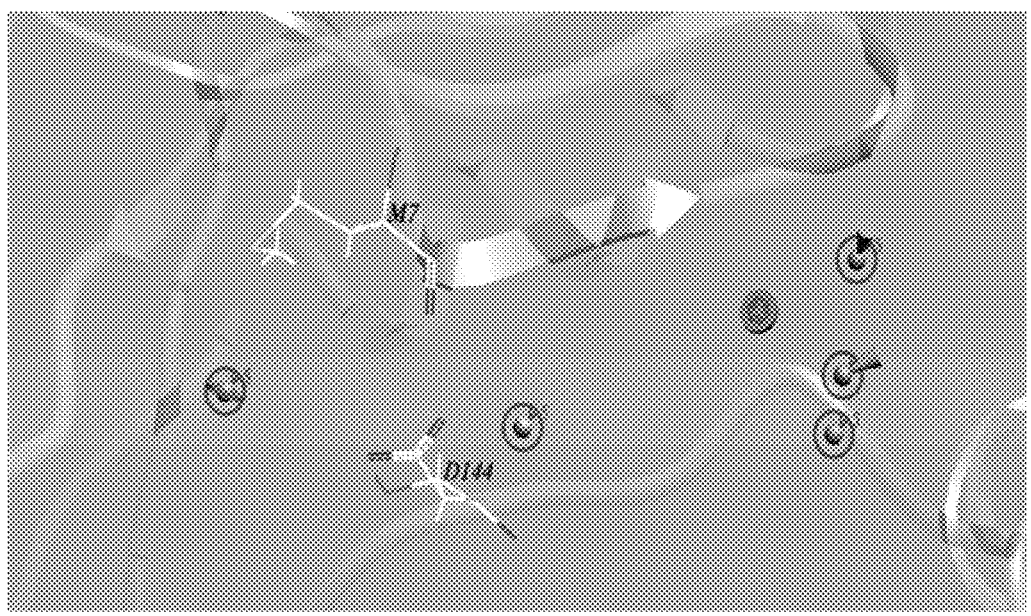
FIG. 6 shows a pharmacophore model for mouse PERK inhibitors showing three structural determinants of selectivity and potency. Equivalently, the amino acid present at these three-dimensional structural locations in human PERK, regardless of whether they are the same amino acids as in this pharmacophore model, may be viewed as structural determinants to distinguish between active and inactive as well as selective and non-selective compounds against human PERK. Pharmacophore features are as shown: orange stands for aromatic, blue stands for hydrophobic, green stands for hydrogen bond acceptor (HBA), pink stands for partial positive charge. The four points on the right (two HBAs, one hydrophobic, and one aromatic) interact with the N-terminal portion of the PERK activation loop area. The point in the middle provides electrostatic complementarity to the residue Asp-144. The point on the left is either aromatic or hydrophobic making contact with Met-7. PERK active site is displayed as ribbon.

Based on the examples described supra, three structural determinants of PERK inhibitor selectivity and potency were identified. A chemical scaffold that fits reasonably well into the PERK active site and has favorable contacts with PERK Met-7 can provide a minimal set of requirements for PERK inhibition. An additional contact with the N-terminal portion of the activation loop is required for such a chemical scaffold to achieve selective inhibition of PERK compared to other kinases. Finally, an additional chemically complementary contact with PERK Asp-144 residue can improve the potency of the selective PERK inhibitor. These three findings draw out a novel, minimal pharmacophore model for PERK inhibitors (FIG. 6).

The experimental validation of the proposed 3D pharmacophore model consists of: 1) the statistically significant differences in eIF2α phosphorylation observed between matched sets of chemically similar compounds that differ only in the groups that are predicted by docking to interact with the key contact points; and 2) the Lineweaver-Burke ATP competition results (FIG. 5) showing that the compounds act competitively at the kinase ATP binding site. The correlation of the docking results with the activity to such a high statistical significance for three different contact points is unlikely to occur without the binding geometry predicted by docking being at least moderately accurate. Nevertheless, crystallization of the compounds with PERK and subsequent x-ray crystallography or structural studies by other methods is the gold standard validation, and the results may reveal additional important features of the pharmacophore model.

Compounds adhering to this model but making additional contacts to increase their potency may be clinically useful as PERK inhibiting anti-cancer and/or anti-Alzheimer's disease drugs. The activation loop in particular offers many additional points of contact for increased selectivity and potency. The unstructured nature of the kinase activation loops hampers rational drug design approaches in the past, however, the present invention shows that a systematic design approach can succeed in targeting this area. Notably, the computational approach used in the present invention allows for the three-dimensional visualization of the atomic interactions between the ligand (e.g., candidate compound(s)) and the receptor/target (e.g., PERK and its relevant fragments), which both resulted in novel inhibitors and a pathway for optimization. For druggable pockets with limited variability between protein species, such as kinase active sites, a 3D approach may be the most productive path to selective inhibitors. The methods described in the present invention could be helpful for the systematic and efficient development of specific and potent PERK inhibitors.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of identifying compounds useful in decreasing protein kinase-like endoplasmic reticulum protein kinase (PERK), said method comprising:
providing a first model consisting of a contiguous amino acid sequence fragment of SEQ ID NO: 1, wherein said contiguous amino acid sequence fragment either (i) begins at amino acid residue Asp144 of SEQ ID NO: 1; (ii) ends at amino acid residue Ser191 of SEQ ID NO: 1; or (iii) begins at amino acid residue Asp144 and ends at amino acid residue Ser191 of SEQ ID NO:1;
providing one or more candidate compounds;
evaluating contact between the candidate compounds and the first model consisting of a contiguous amino acid sequence fragment of SEQ ID NO: 1, wherein said contiguous amino acid sequence fragment either (i) begins at amino acid residue Asp144 of SEQ ID NO: 1; (ii) ends at amino acid residue Ser191 of SEQ ID NO: 1; or (iii) begins at amino acid residue Asp144 and ends at amino acid residue Ser191 of SEQ ID NO:1; and
identifying the compounds which, based on said evaluating, have the ability to bind to a contiguous amino acid sequence fragment of SEQ ID NO: 1, wherein said contiguous amino acid sequence fragment either (i) begins at amino acid residue Asp144 of SEQ ID NO: 1; (ii) ends at amino acid residue Ser191 of SEQ ID NO: 1; or (iii) begins at amino acid residue Asp144 and ends at amino acid residue Ser191 of SEQ ID NO:1, as compounds potentially useful for decreasing PERK.

2. The method of claim 1 further comprising:
providing a second model comprising a peptide comprising amino acid residue Aspartate-144 of SEQ ID NO: 1;
examining contact between the identified candidate compounds and the second model to determine which of the identified candidate compounds have the ability to bind to the second model; and
designating the identified compounds which, based on said examining, have the ability to bind to the second model as compounds with enhanced potential to decrease PERK.

3. The method of claim 2, wherein binding to the second model involves electrostatic complementarity.

4. The method according to claim 1, further comprising:
linking functional groups or molecule fragments in the identified candidate compounds to form de novo compounds.

5. The method according to claim 1, wherein said evaluating comprises using automated docking algorithms.

6. The method of claim 1 further comprising:
screening the identified compounds in vitro for their ability to kill and/or decrease growth of cancer cells and
designating the identified compounds which kill and/or decrease growth of cancer cells as being cancer therapeutics.

7. The method of claim 1, wherein said contiguous amino acid fragment begins at amino acid residue Asp144 of SEQ ID NO: 1.

8. The method of claim 1, wherein said contiguous amino acid fragment ends at amino acid residue Ser191 of SEQ ID NO: 1.

9. The method of claim 1, wherein said contiguous amino acid fragment begins at amino acid residue Asp144 and ends at amino acid residue Ser191 of SEQ ID NO: 1.

* * * * *

SEQUENCE LISTING

```
<160> NUMBER OF SEQ ID NOS: 4

<210> SEQ ID NO 1
<211> LENGTH: 278
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<222> LOCATION: (7)..(7)
<223> OTHER INFORMATION: Xaa can be M or L
<220> FEATURE:
<221> NAME/KEY: MISC_FEATURE
<222> LOCATION: (69)..(69)
<223> OTHER INFORMATION: Xaa can be A or T
<220> FEATURE:
<221> NAME/KEY: MISC_FEATURE
<222> LOCATION: (91)..(91)
<223> OTHER INFORMATION: Xaa can be G or R
<220> FEATURE:
<221> NAME/KEY: MISC_FEATURE
<222> LOCATION: (94)..(94)
<223> OTHER INFORMATION: Xaa can be S or T
<220> FEATURE:
<221> NAME/KEY: MISC_FEATURE
<222> LOCATION: (95)..(95)
<223> OTHER INFORMATION: Xaa can be I or L
<220> FEATURE:
<221> NAME/KEY: MISC_FEATURE
<222> LOCATION: (97)..(97)
<223> OTHER INFORMATION: Xaa can be E or D
<220> FEATURE:
<221> NAME/KEY: MISC_FEATURE
<222> LOCATION: (100)..(100)
<223> OTHER INFORMATION: Xaa can be R or H
<220> FEATURE:
<221> NAME/KEY: MISC_FEATURE
<222> LOCATION: (101)..(101)
<223> OTHER INFORMATION: Xaa can be S or G
<220> FEATURE:
<221> NAME/KEY: MISC_FEATURE
<222> LOCATION: (169)..(169)
<223> OTHER INFORMATION: Xaa can be R or T
<220> FEATURE:
<221> NAME/KEY: MISC_FEATURE
<222> LOCATION: (189)..(189)
<223> OTHER INFORMATION: Xaa can be S or N
<220> FEATURE:
<221> NAME/KEY: MISC_FEATURE
<222> LOCATION: (213)..(213)
<223> OTHER INFORMATION: Xaa can be Q or L
<220> FEATURE:
<221> NAME/KEY: MISC_FEATURE
<222> LOCATION: (219)..(219)
<223> OTHER INFORMATION: Xaa can be T or I
<220> FEATURE:
<221> NAME/KEY: MISC_FEATURE
<222> LOCATION: (230)..(230)
<223> OTHER INFORMATION: Xaa can be P or L
<220> FEATURE:
<221> NAME/KEY: MISC_FEATURE
<222> LOCATION: (238)..(238)
<223> OTHER INFORMATION: Xaa can be Q or C
<220> FEATURE:
<221> NAME/KEY: MISC_FEATURE
<222> LOCATION: (240)..(240)
<223> OTHER INFORMATION: Xaa can be Y or H
<220> FEATURE:
<221> NAME/KEY: MISC_FEATURE
<222> LOCATION: (241)..(241)
```

```
<223> OTHER INFORMATION: Xaa can be V or M
<220> FEATURE:
<221> NAME/KEY: MISC_FEATURE
<222> LOCATION: (252)..(252)
<223> OTHER INFORMATION: Xaa can be M or T
<220> FEATURE:
<221> NAME/KEY: MISC_FEATURE
<222> LOCATION: (258)..(258)
<223> OTHER INFORMATION: Xaa can be I or T
<220> FEATURE:
<221> NAME/KEY: MISC_FEATURE
<222> LOCATION: (259)..(259)
<223> OTHER INFORMATION: Xaa can be N or D
<220> FEATURE:
<221> NAME/KEY: MISC_FEATURE
<222> LOCATION: (265)..(265)
<223> OTHER INFORMATION: Xaa can be V or I
<220> FEATURE:
<221> NAME/KEY: MISC_FEATURE
<222> LOCATION: (268)..(268)
<223> OTHER INFORMATION: Xaa can be D or N
<220> FEATURE:
<221> NAME/KEY: MISC_FEATURE
<222> LOCATION: (270)..(270)
<223> OTHER INFORMATION: Xaa can be D or E

<400> SEQUENCE: 1

Phe Glu Pro Ile Gln Cys Xaa Gly Arg Gly Gly Phe Gly Val Val Phe
1               5                   10                  15

Glu Ala Lys Asn Lys Val Asp Asp Cys Asn Tyr Ala Ile Lys Arg Ile
            20                  25                  30

Arg Leu Pro Asn Arg Glu Leu Ala Arg Glu Lys Val Met Arg Glu Val
        35                  40                  45

Lys Ala Leu Ala Lys Leu Glu His Pro Gly Ile Val Arg Tyr Phe Asn
    50                  55                  60

Ala Trp Leu Glu Xaa Lys Val Tyr Leu Tyr Ile Gln Met Gln Leu Cys
65                  70                  75                  80

Arg Lys Glu Asn Leu Lys Asp Trp Met Asn Xaa Arg Cys Xaa Xaa Glu
                85                  90                  95

Xaa Arg Glu Xaa Xaa Val Cys Leu His Ile Phe Leu Gln Ile Ala Glu
            100                 105                 110

Ala Val Glu Phe Leu His Ser Lys Gly Leu Met His Arg Asp Leu Lys
        115                 120                 125

Pro Ser Asn Ile Phe Phe Thr Met Asp Asp Val Val Lys Val Gly Asp
    130                 135                 140

Phe Gly Leu Val Thr Ala Met Asp Gln Asp Glu Glu Gln Thr Val
145                 150                 155                 160

Leu Thr Pro Met Pro Ala Tyr Ala Xaa His Thr Gly Gln Val Gly Thr
                165                 170                 175

Lys Leu Tyr Met Ser Pro Glu Gln Ile His Gly Asn Xaa Tyr Ser His
            180                 185                 190

Lys Val Asp Ile Phe Ser Leu Gly Leu Ile Leu Phe Glu Leu Leu Tyr
        195                 200                 205

Pro Phe Ser Thr Xaa Met Glu Arg Val Arg Xaa Leu Thr Asp Val Arg
    210                 215                 220

Asn Leu Lys Phe Pro Xaa Leu Phe Thr Gln Lys Tyr Pro Xaa Glu Xaa
225                 230                 235                 240

Xaa Met Val Gln Asp Met Leu Ser Pro Ser Pro Xaa Glu Arg Pro Glu
                245                 250                 255

Ala Xaa Xaa Ile Ile Glu Asn Ala Xaa Phe Glu Xaa Leu Xaa Phe Pro
            260                 265                 270
```

```
Gly Lys Thr Val Leu Arg
        275

<210> SEQ ID NO 2
<211> LENGTH: 278
<212> TYPE: PRT
<213> ORGANISM: Mus musculus

<400> SEQUENCE: 2

Phe Glu Pro Ile Gln Cys Met Gly Arg Gly Phe Gly Val Val Phe
1               5                   10                  15

Glu Ala Lys Asn Lys Val Asp Asp Cys Asn Tyr Ala Ile Lys Arg Ile
            20                  25                  30

Arg Leu Pro Asn Arg Glu Leu Ala Arg Glu Lys Val Met Arg Glu Val
        35                  40                  45

Lys Ala Leu Ala Lys Leu Glu His Pro Gly Ile Val Arg Tyr Phe Asn
    50                  55                  60

Ala Trp Leu Glu Thr Lys Val Tyr Leu Tyr Ile Gln Met Gln Leu Cys
65                  70                  75                  80

Arg Lys Glu Asn Leu Lys Asp Trp Met Asn Arg Arg Cys Ser Leu Glu
                85                  90                  95

Asp Arg Glu His Gly Val Cys Leu His Ile Phe Leu Gln Ile Ala Glu
            100                 105                 110

Ala Val Glu Phe Leu His Ser Lys Gly Leu Met His Arg Asp Leu Lys
        115                 120                 125

Pro Ser Asn Ile Phe Phe Thr Met Asp Asp Val Val Lys Val Gly Asp
    130                 135                 140

Phe Gly Leu Val Thr Ala Met Asp Gln Asp Glu Glu Gln Thr Val
145                 150                 155                 160

Leu Thr Pro Met Pro Ala Tyr Ala Thr His Thr Gly Gln Val Gly Thr
                165                 170                 175

Lys Leu Tyr Met Ser Pro Glu Gln Ile His Gly Asn Asn Tyr Ser His
            180                 185                 190

Lys Val Asp Ile Phe Ser Leu Gly Leu Ile Leu Phe Glu Leu Leu Tyr
        195                 200                 205

Pro Phe Ser Thr Leu Met Glu Arg Val Arg Ile Leu Thr Asp Val Arg
    210                 215                 220

Asn Leu Lys Phe Pro Leu Leu Phe Thr Gln Lys Tyr Pro Gln Glu His
225                 230                 235                 240

Met Met Val Gln Asp Met Leu Ser Pro Ser Pro Thr Glu Arg Pro Glu
                245                 250                 255

Ala Thr Asp Ile Ile Glu Asn Ala Ile Phe Glu Asn Leu Glu Phe Pro
            260                 265                 270

Gly Lys Thr Val Leu Arg
        275

<210> SEQ ID NO 3
<211> LENGTH: 1114
<212> TYPE: PRT
<213> ORGANISM: Mus musculus

<400> SEQUENCE: 3

Met Glu Arg Ala Thr Arg Pro Gly Pro Arg Ala Leu Leu Leu Leu Leu
1               5                   10                  15

Phe Leu Leu Leu Gly Cys Ala Ala Gly Ile Ser Ala Val Ala Pro Ala
            20                  25                  30
```

```
Arg Ser Leu Leu Ala Pro Ala Ser Glu Thr Val Phe Gly Leu Gly Ala
             35                  40                  45

Ala Ala Ala Pro Thr Ser Ala Ala Arg Val Pro Ala Val Ala Thr Ala
 50                  55                  60

Glu Val Thr Val Glu Asp Ala Glu Ala Leu Pro Ala Ala Ala Gly Glu
 65                  70                  75                  80

Pro Glu Ser Arg Ala Thr Glu Pro Asp Asp Val Glu Leu Arg Pro
                 85                  90                  95

Arg Gly Arg Ser Leu Val Ile Ile Ser Thr Leu Asp Gly Arg Ile Ala
                100                 105                 110

Ala Leu Asp Ala Glu Asn Asp Gly Lys Lys Gln Trp Asp Leu Asp Val
            115                 120                 125

Gly Ser Gly Ser Leu Val Ser Ser Ser Leu Ser Lys Pro Glu Val Phe
130                 135                 140

Gly Asn Lys Met Ile Ile Pro Ser Leu Asp Gly Asp Leu Phe Gln Trp
145                 150                 155                 160

Asp Arg Asp Arg Glu Ser Met Glu Ala Val Pro Phe Thr Val Glu Ser
                165                 170                 175

Leu Leu Glu Ser Ser Tyr Lys Phe Gly Asp Asp Val Val Leu Val Gly
                180                 185                 190

Gly Lys Ser Leu Ile Thr Tyr Gly Leu Ser Ala Tyr Ser Gly Lys Leu
            195                 200                 205

Arg Tyr Ile Cys Ser Ala Leu Gly Cys Arg Arg Trp Asp Ser Asp Glu
210                 215                 220

Met Glu Glu Glu Asp Ile Leu Leu Leu Gln Arg Thr Gln Lys Thr
225                 230                 235                 240

Val Arg Ala Val Gly Pro Arg Ser Gly Ser Glu Lys Trp Asn Phe Ser
                245                 250                 255

Val Gly His Phe Glu Leu Arg Tyr Ile Pro Asp Met Glu Thr Arg Ala
            260                 265                 270

Gly Phe Ile Glu Ser Thr Phe Lys Pro Gly Gly Asn Lys Glu Asp Ser
275                 280                 285

Lys Ile Ile Ser Asp Val Glu Glu Gln Glu Ala Thr Met Leu Asp Thr
290                 295                 300

Val Ile Lys Val Ser Val Ala Asp Trp Lys Val Met Ala Phe Ser Arg
305                 310                 315                 320

Lys Gly Gly Arg Leu Glu Trp Glu Tyr Gln Phe Cys Thr Pro Ile Ala
                325                 330                 335

Ser Ala Trp Leu Val Arg Asp Gly Lys Val Ile Pro Ile Ser Leu Phe
            340                 345                 350

Asp Asp Thr Ser Tyr Thr Ala Ser Glu Glu Ala Leu Gly Asp Glu Glu
                355                 360                 365

Asp Ile Val Glu Ala Ala Arg Gly Ala Thr Glu Asn Ser Val Tyr Leu
370                 375                 380

Gly Met Tyr Arg Gly Gln Leu Tyr Leu Gln Ser Ser Val Arg Val Ser
385                 390                 395                 400

Glu Lys Phe Pro Thr Ser Pro Lys Ala Leu Glu Ser Val Asn Gly Glu
                405                 410                 415

Asn Ala Ile Ile Pro Leu Pro Thr Ile Lys Trp Lys Pro Leu Ile His
            420                 425                 430

Ser Pro Ser Arg Thr Pro Val Leu Val Gly Ser Asp Glu Phe Asp Lys
435                 440                 445

Cys Leu Ser Asn Asp Lys Tyr Ser His Glu Glu Tyr Ser Asn Gly Ala
```

```
              450                 455                 460
Leu Ser Ile Leu Gln Tyr Pro Tyr Asp Asn Gly Tyr Tyr Leu Pro Tyr
465                 470                 475                 480

Tyr Lys Arg Glu Arg Asn Lys Arg Ser Thr Gln Ile Thr Val Arg Phe
                485                 490                 495

Leu Asp Ser Pro His Tyr Ser Lys Asn Ile Arg Lys Lys Asp Pro Ile
                500                 505                 510

Leu Leu Leu His Trp Trp Lys Glu Ile Phe Gly Thr Ile Leu Leu Cys
            515                 520                 525

Ile Val Ala Thr Thr Phe Ile Val Arg Arg Leu Phe His Pro Gln Pro
        530                 535                 540

His Arg Gln Arg Lys Glu Ser Glu Thr Gln Cys Gln Thr Glu Ser Lys
545                 550                 555                 560

Tyr Asp Ser Val Ser Ala Asp Val Ser Asp Asn Ser Trp Asn Asp Met
                565                 570                 575

Lys Tyr Ser Gly Tyr Val Ser Arg Tyr Leu Thr Asp Phe Glu Pro Ile
                580                 585                 590

Gln Cys Met Gly Arg Gly Gly Phe Gly Val Val Phe Glu Ala Lys Asn
            595                 600                 605

Lys Val Asp Asp Cys Asn Tyr Ala Ile Lys Arg Ile Arg Leu Pro Asn
        610                 615                 620

Arg Glu Leu Ala Arg Glu Lys Val Met Arg Glu Val Lys Ala Leu Ala
625                 630                 635                 640

Lys Leu Glu His Pro Gly Ile Val Arg Tyr Phe Asn Ala Trp Leu Glu
                645                 650                 655

Thr Pro Pro Glu Lys Trp Gln Glu Glu Met Asp Glu Ile Trp Leu Lys
                660                 665                 670

Asp Glu Ser Thr Asp Trp Pro Leu Ser Ser Pro Ser Pro Met Asp Ala
            675                 680                 685

Pro Ser Val Lys Ile Arg Arg Met Asp Pro Phe Ser Thr Lys Glu Gln
        690                 695                 700

Ile Glu Val Ile Ala Pro Ser Pro Glu Arg Ser Arg Ser Phe Ser Val
705                 710                 715                 720

Gly Ile Ser Cys Gly Gln Thr Ser Ser Glu Ser Gln Phe Ser Pro
                725                 730                 735

Leu Glu Phe Ser Gly Thr Asp Cys Gly Asp Asn Ser Asp Ser Ala Asp
            740                 745                 750

Ala Ala Tyr Asn Leu Gln Asp Ser Cys Leu Thr Asp Cys Glu Asp Val
        755                 760                 765

Glu Asp Gly Thr Val Asp Gly Asn Asp Glu Gly His Ser Phe Glu Leu
770                 775                 780

Cys Pro Ser Glu Ala Ser Pro Tyr Thr Arg Ser Arg Glu Gly Thr Ser
785                 790                 795                 800

Ser Ser Ile Val Phe Glu Asp Ser Gly Cys Gly Asn Ala Ser Ser Lys
                805                 810                 815

Glu Glu Pro Arg Gly Asn Arg Leu His Asp Gly Asn His Tyr Val Asn
            820                 825                 830

Lys Leu Thr Asp Leu Lys Cys Ser Ser Arg Ser Ser Ser Glu Ala
        835                 840                 845

Thr Thr Leu Ser Thr Ser Pro Thr Arg Pro Thr Thr Leu Ser Leu Asp
850                 855                 860

Phe Thr Lys Asn Thr Val Gly Gln Leu Gln Pro Ser Ser Pro Lys Val
865                 870                 875                 880
```

```
Tyr Leu Tyr Ile Gln Met Gln Leu Cys Arg Lys Glu Asn Leu Lys Asp
            885                 890                 895

Trp Met Asn Arg Arg Cys Ser Leu Glu Asp Arg Glu His Gly Val Cys
        900                 905                 910

Leu His Ile Phe Leu Gln Ile Ala Glu Ala Val Glu Phe Leu His Ser
    915                 920                 925

Lys Gly Leu Met His Arg Asp Leu Lys Pro Ser Asn Ile Phe Phe Thr
930                 935                 940

Met Asp Asp Val Val Lys Val Gly Asp Phe Gly Leu Val Thr Ala Met
945                 950                 955                 960

Asp Gln Asp Glu Glu Gln Thr Val Leu Thr Pro Met Pro Ala Tyr
                965                 970                 975

Ala Thr His Thr Gly Gln Val Gly Thr Lys Leu Tyr Met Ser Pro Glu
            980                 985                 990

Gln Ile His Gly Asn Asn Tyr Ser His Lys Val Asp Ile Phe Ser Leu
        995                 1000                1005

Gly Leu Ile Leu Phe Glu Leu Leu Tyr Pro Phe Ser Thr Gln Met
    1010                1015                1020

Glu Arg Val Arg Ile Leu Thr Asp Val Arg Asn Leu Lys Phe Pro
    1025                1030                1035

Leu Leu Phe Thr Gln Lys Tyr Pro Gln Glu His Met Met Val Gln
    1040                1045                1050

Asp Met Leu Ser Pro Ser Pro Thr Glu Arg Pro Glu Ala Thr Asp
    1055                1060                1065

Ile Ile Glu Asn Ala Ile Phe Glu Asn Leu Glu Phe Pro Gly Lys
    1070                1075                1080

Thr Val Leu Arg Gln Arg Ser Arg Ser Met Ser Ser Ser Gly Thr
    1085                1090                1095

Lys His Ser Arg Gln Pro Ser Cys Ser Tyr Ser Pro Leu Pro Gly
    1100                1105                1110

Asn

<210> SEQ ID NO 4
<211> LENGTH: 1115
<212> TYPE: PRT
<213> ORGANISM: Homo sapiens

<400> SEQUENCE: 4

Met Glu Arg Ala Ile Ser Pro Gly Leu Leu Val Arg Ala Leu Leu Leu
1               5                   10                  15

Leu Leu Leu Leu Gly Leu Ala Ala Arg Thr Val Ala Ala Gly Arg Ala
            20                  25                  30

Arg Gly Leu Pro Ala Pro Thr Ala Glu Ala Ala Phe Gly Leu Gly Ala
        35                  40                  45

Ala Ala Ala Pro Thr Ser Ala Thr Arg Val Pro Ala Ala Gly Ala Val
    50                  55                  60

Ala Ala Ala Glu Val Thr Val Glu Asp Ala Glu Ala Leu Pro Ala Ala
65                  70                  75                  80

Ala Gly Glu Gln Glu Pro Arg Pro Glu Pro Asp Asp Glu Thr Glu
                85                  90                  95

Leu Arg Pro Arg Gly Arg Ser Leu Val Ile Ile Ser Thr Leu Asp Gly
            100                 105                 110

Arg Ile Ala Ala Leu Asp Pro Glu Asn His Gly Lys Lys Gln Trp Asp
        115                 120                 125
```

```
Leu Asp Val Gly Ser Gly Ser Leu Val Ser Ser Leu Ser Lys Pro
    130                 135                 140

Glu Val Phe Gly Asn Lys Met Ile Ile Pro Ser Leu Asp Gly Ala Leu
145                 150                 155                 160

Phe Gln Trp Asp Arg Asp Arg Glu Ser Met Glu Thr Val Pro Phe Thr
                165                 170                 175

Val Glu Ser Leu Leu Glu Ser Ser Tyr Lys Phe Gly Asp Asp Val Val
                180                 185                 190

Leu Val Gly Gly Lys Ser Leu Thr Thr Tyr Gly Leu Ser Ala Tyr Ser
            195                 200                 205

Gly Lys Val Arg Tyr Ile Cys Ser Ala Leu Gly Cys Arg Gln Trp Asp
        210                 215                 220

Ser Asp Glu Met Glu Gln Glu Asp Ile Leu Leu Leu Gln Arg Thr
225                 230                 235                 240

Gln Lys Thr Val Arg Ala Val Gly Pro Arg Ser Gly Asn Glu Lys Trp
                245                 250                 255

Asn Phe Ser Val Gly His Phe Glu Leu Arg Tyr Ile Pro Asp Met Glu
                260                 265                 270

Thr Arg Ala Gly Phe Ile Glu Ser Thr Phe Lys Pro Asn Glu Asn Thr
            275                 280                 285

Glu Glu Ser Lys Ile Ile Ser Asp Val Glu Glu Gln Glu Ala Ala Ile
        290                 295                 300

Met Asp Ile Val Ile Lys Val Ser Val Ala Asp Trp Lys Val Met Ala
305                 310                 315                 320

Phe Ser Lys Lys Gly Gly His Leu Glu Trp Glu Tyr Gln Phe Cys Thr
                325                 330                 335

Pro Ile Ala Ser Ala Trp Leu Leu Lys Asp Gly Lys Val Ile Pro Ile
                340                 345                 350

Ser Leu Phe Asp Asp Thr Ser Tyr Thr Ser Asn Asp Val Leu Glu
            355                 360                 365

Asp Glu Glu Asp Ile Val Glu Ala Ala Arg Gly Ala Thr Glu Asn Ser
    370                 375                 380

Val Tyr Leu Gly Met Tyr Arg Gly Gln Leu Tyr Leu Gln Ser Ser Val
385                 390                 395                 400

Arg Ile Ser Glu Lys Phe Pro Ser Ser Pro Lys Ala Leu Glu Ser Val
                405                 410                 415

Thr Asn Glu Asn Ala Ile Ile Pro Leu Pro Thr Ile Lys Trp Lys Pro
                420                 425                 430

Leu Ile His Ser Pro Ser Arg Thr Pro Val Leu Val Gly Ser Asp Glu
        435                 440                 445

Phe Asp Lys Cys Leu Ser Asn Asp Lys Phe Ser His Glu Glu Tyr Ser
    450                 455                 460

Asn Gly Ala Leu Ser Ile Leu Gln Tyr Pro Tyr Asp Asn Gly Tyr Tyr
465                 470                 475                 480

Leu Pro Tyr Tyr Lys Arg Glu Arg His Lys Arg Ser Thr Gln Ile Thr
                485                 490                 495

Val Arg Phe Leu Asp Asn Pro His Tyr Asn Lys Asn Ile Arg Lys Lys
                500                 505                 510

Asp Pro Val Leu Leu Leu His Trp Trp Lys Glu Ile Val Ala Thr Ile
        515                 520                 525

Leu Phe Cys Ile Ile Ala Thr Thr Phe Ile Val Arg Arg Leu Phe His
    530                 535                 540
```

```
Pro His Pro His Arg Gln Arg Lys Glu Ser Glu Thr Gln Cys Gln Thr
545                 550                 555                 560

Glu Asn Lys Tyr Asp Ser Val Ser Gly Glu Ala Asn Asp Ser Ser Trp
                565                 570                 575

Asn Asp Ile Lys Asn Ser Gly Tyr Ile Ser Arg Tyr Leu Thr Asp Phe
            580                 585                 590

Glu Pro Ile Gln Cys Leu Gly Arg Gly Gly Phe Gly Val Val Phe Glu
        595                 600                 605

Ala Lys Asn Lys Val Asp Asp Cys Asn Tyr Ala Ile Lys Arg Ile Arg
    610                 615                 620

Leu Pro Asn Arg Glu Leu Ala Arg Glu Lys Val Met Arg Glu Val Lys
625                 630                 635                 640

Ala Leu Ala Lys Leu Glu His Pro Gly Ile Val Arg Tyr Phe Asn Ala
                645                 650                 655

Trp Leu Glu Ala Pro Pro Glu Lys Trp Gln Glu Lys Met Asp Glu Ile
                660                 665                 670

Trp Leu Lys Asp Glu Ser Thr Asp Trp Pro Leu Ser Ser Pro Ser Pro
            675                 680                 685

Met Asp Ala Pro Ser Val Lys Ile Arg Arg Met Asp Pro Phe Ser Thr
        690                 695                 700

Lys Glu His Ile Glu Ile Ile Ala Pro Ser Pro Gln Arg Ser Arg Ser
705                 710                 715                 720

Phe Ser Val Gly Ile Ser Cys Asp Gln Thr Ser Ser Glu Ser Gln
                725                 730                 735

Phe Ser Pro Leu Glu Phe Ser Gly Met Asp His Glu Asp Ile Ser Glu
                740                 745                 750

Ser Val Asp Ala Ala Tyr Asn Leu Gln Asp Ser Cys Leu Thr Asp Cys
            755                 760                 765

Asp Val Glu Asp Gly Thr Met Asp Gly Asn Asp Glu Gly His Ser Phe
        770                 775                 780

Glu Leu Cys Pro Ser Glu Ala Ser Pro Tyr Val Arg Ser Arg Glu Arg
785                 790                 795                 800

Thr Ser Ser Ser Ile Val Phe Glu Asp Ser Gly Cys Asp Asn Ala Ser
                805                 810                 815

Ser Lys Glu Glu Pro Lys Thr Asn Arg Leu His Ile Gly Asn His Cys
                820                 825                 830

Ala Asn Lys Leu Thr Ala Phe Lys Pro Thr Ser Ser Lys Ser Ser Ser
            835                 840                 845

Glu Ala Thr Leu Ser Ile Ser Pro Pro Arg Pro Thr Thr Leu Ser Leu
        850                 855                 860

Asp Leu Thr Lys Asn Thr Thr Glu Lys Leu Gln Pro Ser Ser Pro Lys
865                 870                 875                 880

Val Tyr Leu Tyr Ile Gln Met Gln Leu Cys Arg Lys Glu Asn Leu Lys
                885                 890                 895

Asp Trp Met Asn Gly Arg Cys Thr Ile Glu Glu Arg Gly Arg Ser Val
                900                 905                 910

Cys Leu His Ile Phe Leu Gln Ile Ala Glu Ala Val Glu Phe Leu His
            915                 920                 925

Ser Lys Gly Leu Met His Arg Asp Leu Lys Pro Ser Asn Ile Phe Phe
        930                 935                 940

Thr Met Asp Asp Val Val Lys Val Gly Asp Phe Gly Leu Val Thr Ala
945                 950                 955                 960

Met Asp Gln Asp Glu Glu Glu Gln Thr Val Leu Thr Pro Met Pro Ala
```

-continued

```
               965                 970                 975
Tyr Ala Arg His Thr Gly Gln Val Gly Thr Lys Leu Tyr Met Ser Pro
            980                 985                 990

Glu Gln Ile His Gly Asn Ser Tyr Ser His Lys Val Asp Ile Phe Ser
            995                 1000                1005

Leu Gly Leu Ile Leu Phe Glu Leu Leu Tyr Pro Phe Ser Thr Gln
    1010                1015                1020

Met Glu Arg Val Arg Thr Leu Thr Asp Val Arg Asn Leu Lys Phe
    1025                1030                1035

Pro Pro Leu Phe Thr Gln Lys Tyr Pro Cys Glu Tyr Val Met Val
    1040                1045                1050

Gln Asp Met Leu Ser Pro Ser Pro Met Glu Arg Pro Glu Ala Ile
    1055                1060                1065

Asn Ile Ile Glu Asn Ala Val Phe Glu Asp Leu Asp Phe Pro Gly
    1070                1075                1080

Lys Thr Val Leu Arg Gln Arg Ser Arg Ser Leu Ser Ser Ser Gly
    1085                1090                1095

Thr Lys His Ser Arg Gln Ser Asn Asn Ser His Ser Pro Leu Pro
    1100                1105                1110

Ser Asn
    1115
```